United States Patent
Hatamian et al.

(10) Patent No.: US 11,389,632 B2
(45) Date of Patent: Jul. 19, 2022

(54) INTRADERMAL DRUG DELIVERY DEVICE

(71) Applicant: Mediccene Inc., Mission Viejo, CA (US)

(72) Inventors: Mehdi Hatamian, Mission Viejo, CA (US); Mehrtash Ghalebi, Irvine, CA (US)

(73) Assignee: Mediccene Inc., Mission Viejo, CA (US)

( * ) Notice: Subject to any disclaimer, the term of this patent is extended or adjusted under 35 U.S.C. 154(b) by 0 days.

(21) Appl. No.: 17/557,862

(22) Filed: Dec. 21, 2021

(65) Prior Publication Data

US 2022/0193385 A1    Jun. 23, 2022

Related U.S. Application Data

(60) Provisional application No. 63/128,738, filed on Dec. 21, 2020.

(51) Int. Cl.
| | |
|---|---|
| *A61M 37/00* | (2006.01) |
| *A61M 5/145* | (2006.01) |
| *A61M 5/158* | (2006.01) |
| *A61M 5/172* | (2006.01) |

(52) U.S. Cl.
CPC .... *A61M 37/0015* (2013.01); *A61M 5/14526* (2013.01); *A61M 5/158* (2013.01); *A61M 5/172* (2013.01); *A61M 2037/0023* (2013.01); *A61M 2205/3306* (2013.01); *A61M 2205/3317* (2013.01); *A61M 2205/3327* (2013.01); *A61M 2205/3344* (2013.01); *A61M 2205/3569* (2013.01); *A61M 2205/59* (2013.01)

(58) Field of Classification Search
CPC .......... A61M 37/0015; A61M 5/14526; A61M 5/158; A61M 5/172; A61M 2037/0023; A61M 2205/3306; A61M 2205/3317; A61M 2205/3327; A61M 2205/3344; A61M 2205/3569; A61M 2205/59
See application file for complete search history.

(56) References Cited

U.S. PATENT DOCUMENTS

| | | | |
|---|---|---|---|
| 8,554,317 | B2 | 10/2013 | Duan |
| 8,758,298 | B2 | 6/2014 | Cantor et al. |
| 8,784,363 | B2 | 7/2014 | Frederickson et al. |
| 8,821,779 | B2 | 9/2014 | Ferguson et al. |

(Continued)

*Primary Examiner* — Amber R Stiles
(74) *Attorney, Agent, or Firm* — Makoui Law, PC; Ali Makoui

(57) ABSTRACT

An intradermal fluid delivery device that uses a processor controlled electromechanical delivery mechanism is provided. An air pump pushes fluid containing medication or saline from a fluid compartment through a microneedle array into a person's skin. The processor repeatedly turns the air pump on or off, for the fluid to gradually be injected into the person's skin. The processor may be configured to control the total fluid delivery time as well as the granularity of the fluid delivery. The total fluid delivery time may be set to T, and the time period T may be divided into smaller periods $t_1$ to $t_n$, where the fluid may be administered in a period t1, the fluid delivery may then be stopped for a period t2, followed by another fluid delivery period, etc. The periods t1 to tn may be the same or of different lengths.

20 Claims, 13 Drawing Sheets

(56) References Cited

U.S. PATENT DOCUMENTS

| | | |
|---|---|---|
| 9,119,945 B2 | 9/2015 | Simons et al. |
| 9,174,035 B2 | 11/2015 | Ringsred et al. |
| 9,682,222 B2 | 6/2017 | Burton et al. |
| 9,782,574 B2 | 10/2017 | Simmers |
| 9,789,249 B2 | 10/2017 | Frederickson et al. |
| 9,789,299 B2 | 10/2017 | Simmers |
| 9,872,975 B2 | 1/2018 | Burton et al. |
| 9,895,520 B2 | 2/2018 | Burton et al. |
| 10,010,706 B2 | 7/2018 | Gonzalez et al. |
| 10,010,707 B2 | 7/2018 | Colburn et al. |
| 10,099,043 B2 | 10/2018 | Berry et al. |
| 10,105,524 B2 | 10/2018 | Meyer et al. |
| 10,201,691 B2 | 2/2019 | Berry et al. |
| 10,232,157 B2 | 3/2019 | Berry et al. |
| 10,300,260 B2 | 5/2019 | Wirtanen et al. |
| 10,307,578 B2 | 6/2019 | Frederickson et al. |
| 10,398,885 B2 | 9/2019 | Frits et al. |
| 10,406,339 B2 | 9/2019 | Simmers |
| 10,384,047 B2 | 10/2019 | Simmers |
| 10,391,290 B2 | 10/2019 | Burton et al. |
| 10,549,079 B2 | 2/2020 | Burton et al. |
| 10,576,257 B2 | 3/2020 | Berry et al. |
| 10,695,547 B2 | 6/2020 | Burton et al. |
| 2008/0015494 A1* | 1/2008 | Santini, Jr. ........ A61M 37/0015 604/65 |

* cited by examiner

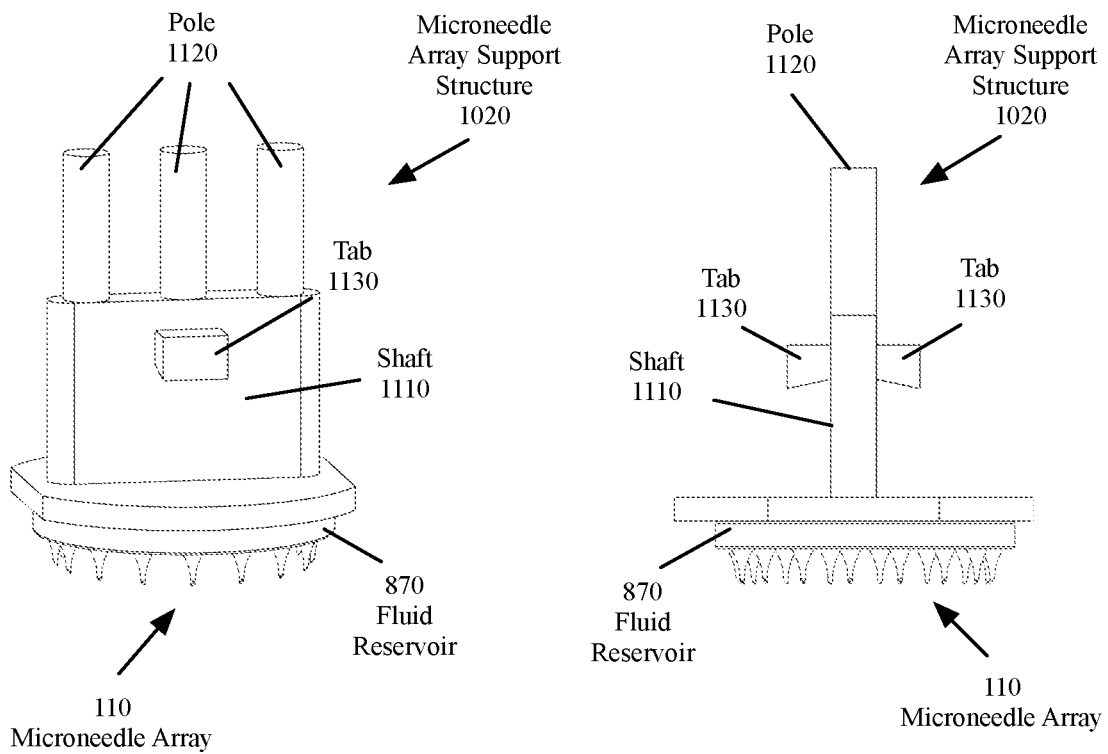
FIG. 11A
FIG. 11B
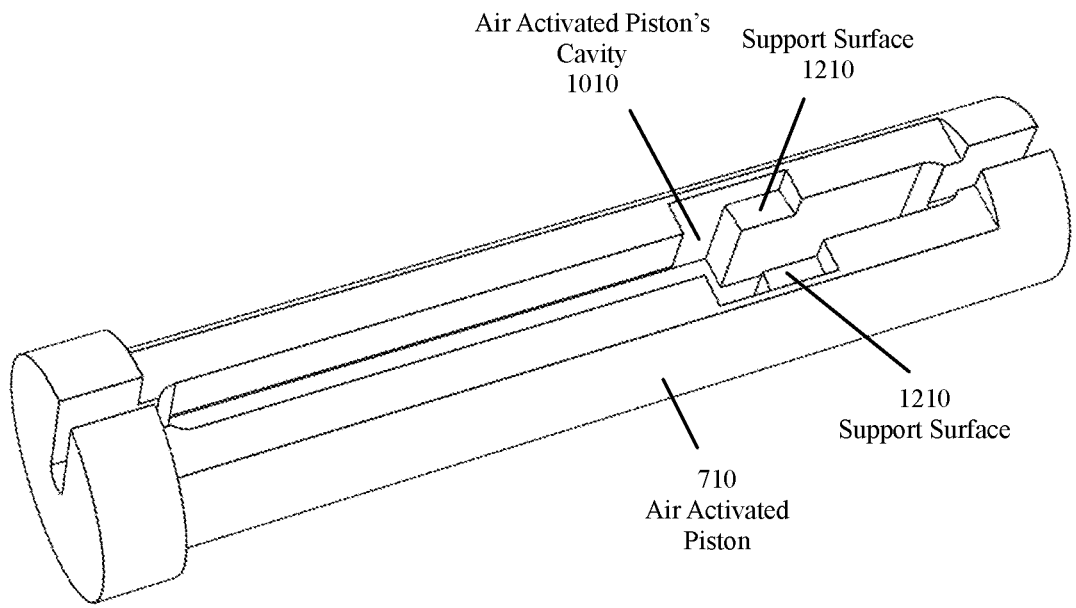
FIG. 12

INTRADERMAL DRUG DELIVERY DEVICE

CLAIM OF BENEFIT TO PRIOR APPLICATIONS

This application claims the benefit of U.S. Provisional Patent Application Ser. No. 63/128,738, filed on Dec. 21, 2020. The contents of U.S. Provisional Patent Application 63/128,738 are hereby incorporated by reference.

BACKGROUND

Intradermal fluid delivery is a method of injecting fluids, such drugs, saline solutions, and nutrition, through the skin instead of the intramuscular or subcutaneous methods. According to the World Health Organization (WHO), the dermis and epidermis of human skin are rich in antigen-presenting cells that make the delivery of vaccines to these layers more efficient than the delivery through the muscle and subcutaneous tissues. The delivery of vaccines through the dermis and epidermis of skin may induce protective immune responses with smaller amount of vaccine antigen. Small applicators referred to as microneedles may be used for the intradermal fluid delivery.

BRIEF DESCRIPTION OF THE DRAWINGS

The various embodiments of the present intradermal fluid delivery device now will be discussed in detail with an emphasis on highlighting the advantageous features. These embodiments depict the novel and non-obvious intradermal fluid delivery device shown in the accompanying drawings, which are for illustrative purposes only. These drawings include the following figures, in which like numerals indicate like parts:

FIG. 11A is a side perspective view and FIG. 11B is a front perspective view of the microneedle array support structure of FIG. 10, according to various aspects of the present embodiments;

FIG. 12 is a top perspective view of the air activated piston of FIG. 10, according to various aspects of the present embodiments;

DETAILED DESCRIPTION

Figure 1:
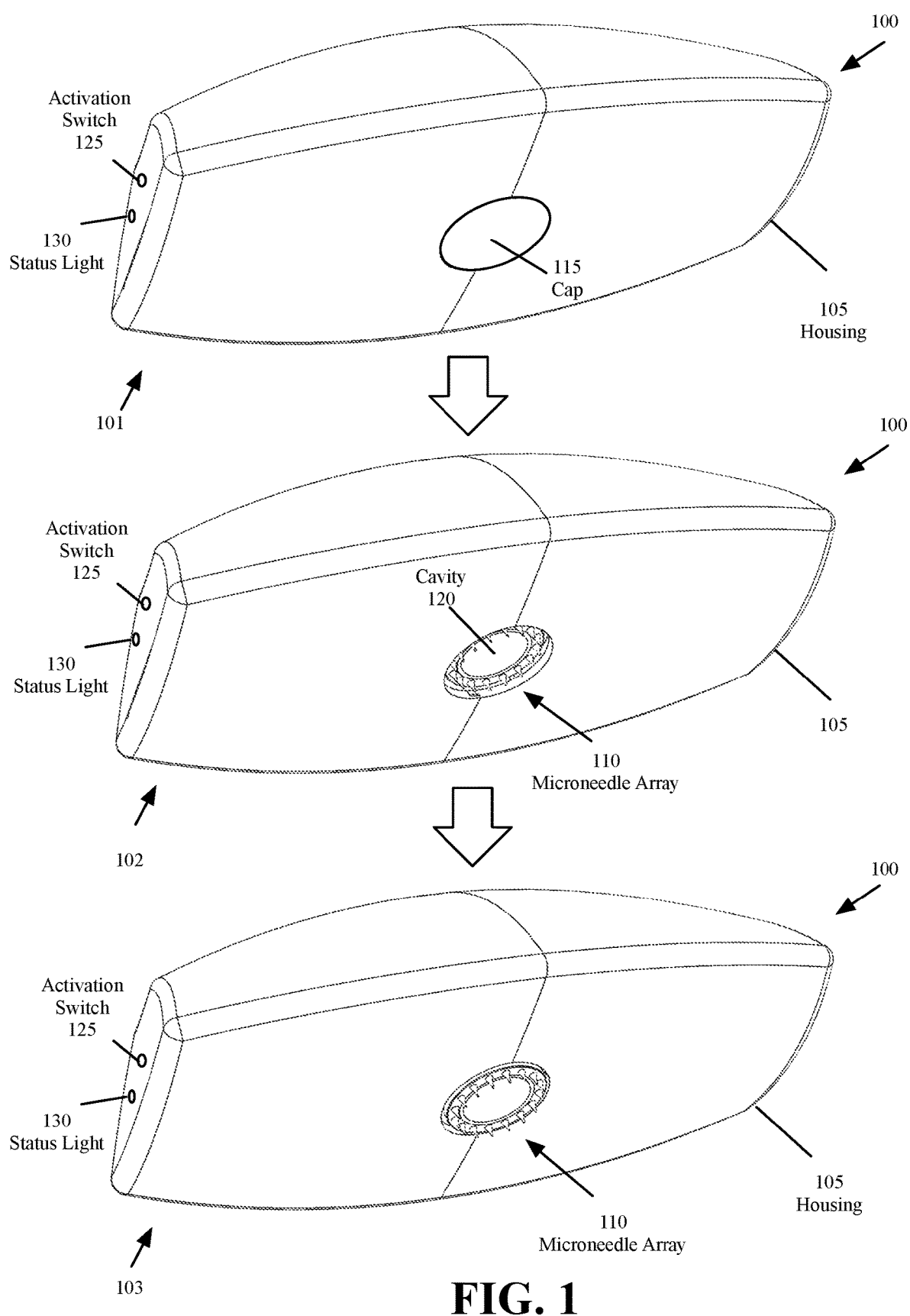
FIG. 1 illustrates a bottom perspective view of an example intradermal fluid delivery device, according to various aspects of the present disclosure.

One aspect of the present embodiments includes the realization that the existing intradermal fluid delivery devices use a mechanical activation mechanism to deliver the fluid. These devices include an activation button. When the activation button is pushed, a spring is released, and the fluid is pushed from a reservoir into a pipe that is connected to a microneedle array. The fluid is delivered through the microneedle array with no control. In these devices it is not possible to precisely control the fluid delivery duration or the rate of administration.

Some of the present embodiments solve the aforementioned problem by providing an intradermal fluid delivery device that uses a processor controlled electromechanical delivery mechanism. An air pump may be used to push fluid from a fluid compartment into a tubing and a microneedle array into a person's skin. The processor may be configured to repeatedly turn the air pump on or off, in order for the fluid to gradually be transferred from the fluid compartment, through the tubing and the microneedle array, into the person's skin. The processor may be configured not only to control the total fluid delivery time but also the granularity of the fluid delivery. The total fluid delivery time may be set to T, and the time period T may be divided into smaller periods $t_1$ to $t_n$, where the fluid may be administered in a period t1, the fluid delivery may then be stopped for a period t2, followed by another fluid delivery period, etc. The periods t1 to tn may be the same or of different lengths. The processor, in some embodiments, may be configured to control the fluid delivery rate (e.g., the volume per second rate of the fluid delivery) for each individual fluid delivery period.

The controlled mode delivery of the present embodiments allows for the flexibility of the step-by-step delivery of vaccines and other type of fluids and provides the technical advantage of allowing the skin to absorb a very small dose (e.g., a micro-dose) of the fluid before delivering the next micro-dose. Each vaccine or fluid may have its own delivery duration and delivery rate requirements, which may be programmed into the intradermal fluid delivery device of the present embodiments. The programming may be done at the manufacture time, at the shipment time, or in the field using an application program running on an external electronic device that is wirelessly connected to the intradermal fluid delivery device. The application program may provide a user interface with options to program the total duration of the fluid delivery, the number of fluid delivery periods and fluid stoppage periods, and the duration of each individual fluid delivery period and fluid stoppage period. The programming provides control over the total duration of fluid delivery and the fluid delivery rate. The delivery rate may be programmed to stay constant by selecting the same amount of time for all fluid delivery periods and the same amount of time for all fluid stoppage periods. Alternatively, each fluid delivery period and each fluid stoppage period may individually be programmed.

Another aspect of the present embodiments includes the realization that the existing intradermal fluid delivery devices do not adjust the fluid delivery parameters of the device based on the softness of a person's skin.

Some of the present embodiments solve the aforementioned problem by providing an intradermal fluid delivery device that includes one or more sensors that measure the skin softness of a person before applying the microneedle array. The intradermal fluid delivery device parameters, such as the delivery time may be adjusted based on the measured skin softness value. Some embodiments may use a light source and a light sensor positioned inside a cavity to measure the skin softness. Some embodiments may use a shaft, a spring, and a pressure sensor to measure the skin softness. Some embodiments may use a shaft, a spring, and a potentiometer to measure the skin softness. Some embodiments may use a shaft, a magnet, a spring, and a Hall effect sensor to measure the skin softness.

Another aspect of the present embodiments includes the realization that the existing intradermal fluid delivery devices do not detect whether the device is evenly attached to a person's skin.

Some of the present embodiments solve the aforementioned problem by providing an intradermal fluid delivery device that includes one or more evenness sensors at the bottom of the device's housing to detect whether the device is evenly placed on a person's skin before the fluid delivery may start. The sensors may be switches or pressure sensors integrated in the bottom of the device. For instance, some embodiments may include two pressure sensors on two opposite sides of the cavity where the microneedle array is located. The sensors may measure the pressure applied by the device to the skin. The processor may receive the measurements from the pressure sensors and may compare the measurements. If the measurements received from the two sensors are not within a threshold of each other, the processor may not start the fluid delivery mechanism even if the fluid delivery mechanism is triggered. When the evenness sensor measurements indicate that the device is not evenly positioned on the skin, the processor(s) of the device may provide an alert through the status light, with audible signals, and/or by sending one or more signals through a wireless interface to external electronic devices. In some embodiments, more than two evenly distributed pressure sensors may be included around the cavity of the microneedle array. The outputs of these sensors may be processed by the processor to determine whether the device is evenly placed on the skin in all directions.

Another aspect of the present embodiments includes the realization that the existing intradermal fluid delivery devices do not detect leaks during the fluid delivery.

Some of the present embodiments solve the aforementioned problem by providing an intradermal fluid delivery device that includes an absorption pad around the microneedle array to absorb any leaks that may occur during the fluid delivery. The absorption pad may be monitored during the fluid delivery to sense the leak. The processor may generate an alarm that may be reported through the status light, by audio signals, and/or by sending one or more signals through a wireless interface to external electronic devices. Some embodiments may measure the impedance between one or more pairs of points on the absorption pad. When there is a leak and the pad gets wet, the impedance between the two points in at least some of the point pairs drops. The processor may compare the impedance between the two points with a threshold and may determine that the device is leaking when the impedance measurement is below the threshold. In addition to, or in lieu of measuring the impedance, the absorption pad's fabric, in some embodiments, may be made of a hydrochromic material that changes color when the absorption pad gets wet.

The remaining detailed description describes the present embodiments with reference to the drawings. In the drawings, reference numbers label elements of the present embodiments. These reference numbers are reproduced below in connection with the discussion of the corresponding drawing features.

FIG. 1 illustrates a bottom perspective view of an example intradermal fluid delivery device 100, according to various aspects of the present disclosure. With reference to FIG. 1, the intradermal fluid delivery device 100 may include a housing 105 that encompasses and secures the fluid compartment (e.g., a cartridge or vial) and the fluid delivery system of the present embodiments.

The term fluid used in this disclosure refers to liquids and solutions, such as, for example, and without limitations, drugs as well as nutrition, sugar, or saline solutions that may not typically be classified as drugs or medications. Example uses of the intradermal drug delivery device 100 of the present embodiments include administrating vaccines or antibiotics through a person's skin. Accordingly, the terms fluid and drug may be used interchangeably in this disclosure. The intradermal fluid delivery device 100 may be used at home or at a point of care.

FIG. 1, as shown, includes three operational steps 101-103. In step 101, a cap 115 may be securing the access to the cavity that houses the microneedle array of the intradermal fluid delivery device 100. The cap 115 may only be removed when the fluid contained in the device 100 is to be administered to a person.

In step 102, the cap 115 may be removed prior to attaching the device 100 to a person's skin. As shown, the device 100 may include a microneedle array 110. The microneedle array 110, in step 102 is inside the microneedle array cavity 120 to facilitate attaching the device 100 to the person's body. As described below, the intradermal fluid delivery device 100 provides a controlled fluid delivery system that may be programmed to deliver the fluid contained in the device 100 over a time period that may depend on the type of the fluid, the skin condition, and/or the age of the person receiving the fluid, etc. It may, therefore, take many seconds to deliver the fluid and it may not be practical to manually hold the device against the person's body.

The device 100, in some embodiments, may include one or more straps (not shown) and/or hook-and-loop fasteners (not shown) to allow the device 100 to be attached to a person's body. An example of the hook-and-loop fasteners is the hook-and-loop fasteners provided by Velcro company.

The device 100 may be attached to a person's arm, abdominal area, etc., such that the microneedle array cavity 120 is evenly placed on the person's skin. Some embodiments may include adhesive on the backing of at least a portion of the strap(s)/fastener(s) to facilitate securing the device to a person's body.

In step 103, the microneedle array 110 may be deployed to deliver the fluid contained in the device 100 into the person's skin (the body of the person is not shown). The device 100, in some embodiments, may include an activation switch 125 that may be used to deploy the microneedle array 110. In addition to, or in lieu of the activation switch 125, some embodiments may include a wireless transceiver (e.g., and without limitations, a Bluetooth transceiver, a Wi-Fi-transceiver, etc.) that may receive one or more signals from an external electronic device to deploy the microneedle array 110.

The intradermal fluid delivery device 100 may be configured such that the microneedle array 110 may not extend more than a predetermined distance from the housing 100 in order to control the penetration of the microneedles into the person's skin. As described below with reference to FIG. 15, the microneedle array cavity 120 may include one or more landing edges and the microneedle assembly may include a ridge that may rest on the landing edge(s) to prevent the microneedle array 110 to extend out more than a predetermined distance from the housing 105.

Some embodiments may include a status light 130 that may display the device's status with different colors, with blinking, and/or by being on or off. In addition to, or in lieu of, the status light 130, some embodiments may provide audible signals through an integrated speaker and/or may send one or more signals to external devices through a wireless interface to indicate the device's status. The status of the device may include, for example, and without limitations, ready to administer the fluid, fluid being administered, fluid administration complete, error status, whether or not the device is positioned evenly on a person's skin, etc.

Figure 2:
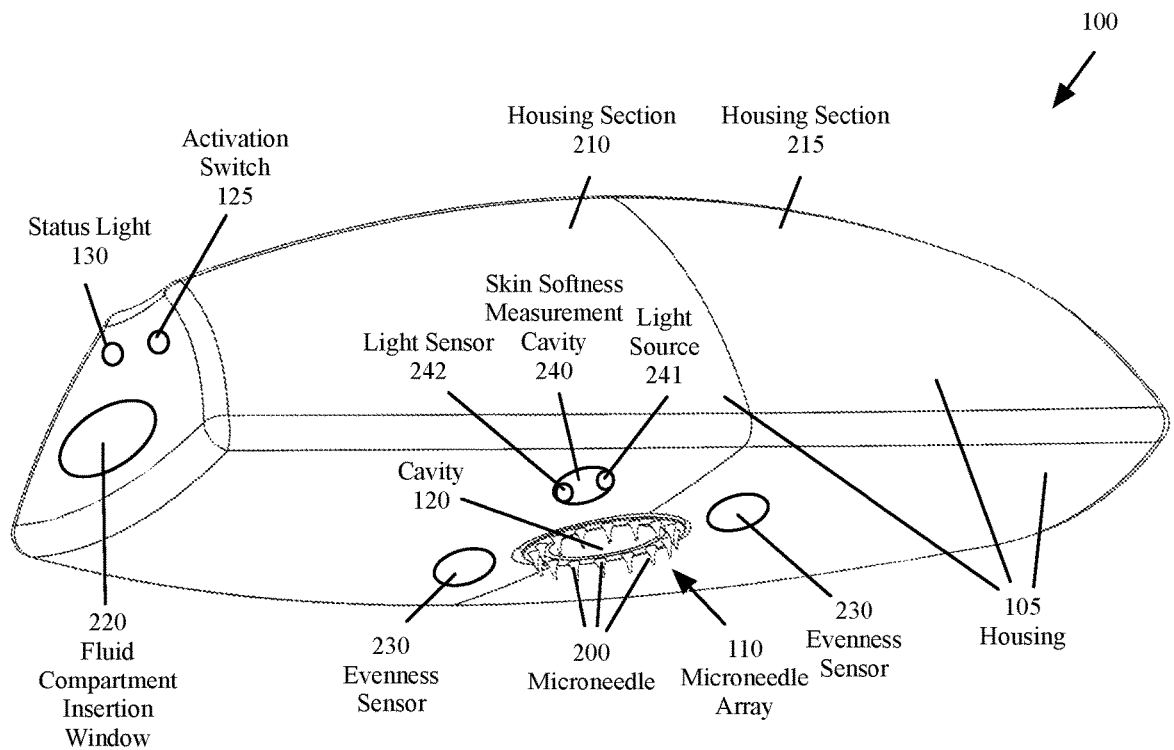
FIGS. 2 and 3A illustrate side perspective views of the intradermal fluid delivery device 1, according to various aspects of the present disclosure.
Figure 3A:
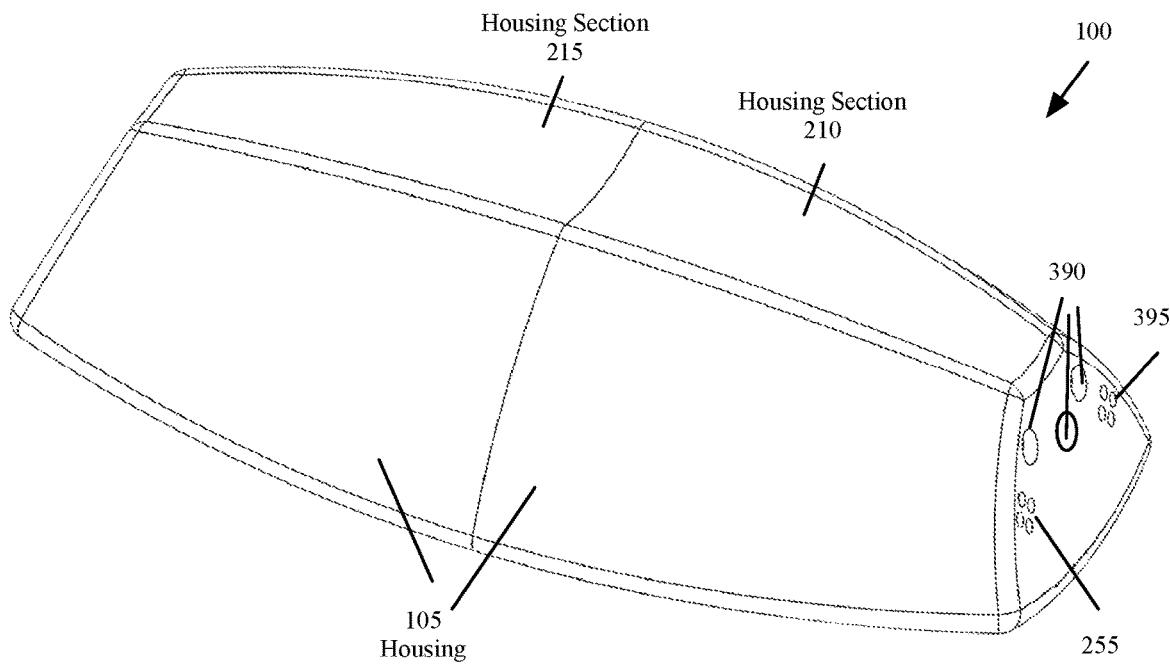

FIGS. 2 and 3A illustrate side perspective views of the intradermal fluid delivery device of FIG. 1, according to various aspects of the present disclosure. With reference to FIGS. 2 and 3A, the housing 105 may include several sections 210-215 that may be permanently sealed after the fluid compartment (not shown) is inserted in the device 100. The housing sections 210-215 may be permanently connected together by adhesives, by one-way insertion tabs, etc., to make the device tamperproof.

In some embodiments, the fluid administered by the device 100 may require refrigeration and/or may have a short expiration time. In these embodiments, the fluid compartment may not be inserted in the device 100 at the time of the device's manufacturing. The device 100, in some embodiments, may include a fluid compartment insertion window 220.

The fluid compartment, in these embodiments, may be inserted through the fluid compartment insertion window 220, which may then be permanently sealed. In other embodiments, when the fluid is not refrigerated and/or has a long expiration date, the fluid compartment may be inserted in the device 100 before the housing sections 210-215 are permanently sealed. Yet in some embodiments, the fluid compartment insertion window 220 may not be permanently sealed to allow the fluid compartment to be inserted into the device 100 at the time of the administration of the fluid to a person. The microneedle array 110 may include several microneedles 200. FIG. 2 shows that the microneedles 200 are arranged in a circular shape in the microneedle array 110. In other embodiments, the microneedles 200 may be arranged in any arbitrary shape.

As shown in FIG. 3A, some embodiments may include several light sources 390 (only three lights are shown for clarity) and one or more openings 395 to allow sound from a small speaker (not shown) inside the housing 105 to reach out. As described below, some embodiments may play musical notes and create lighting patterns when the delivery is done or during the delivery. This option may be useful for using the device on small children and adding an entertainment element to distract them from the fear of getting a vaccine or fluid shot and making it more fun for them. In some embodiments, the speaker and the openings 395 may be used by the processor(s) of the device to generate audio alerts and/or voice messages.

The intradermal fluid delivery device 100 may include one or more evenness sensors 230 at the bottom of the housing 105 to detect whether the device 100 is evenly placed on a person's skin before the fluid delivery may start. The sensor(s) 200 may be, for example, and without limitations, switch(es) or pressure sensor(s) integrated in the bottom of the device 100.

For instance, some embodiments may include two pressure sensors 230 on two opposite sides of the microneedle array cavity 120 where the microneedle array 110 is located. The sensors 230 may measure the pressure applied by the device 100 to the skin. As described below with reference to FIGS. 4-7, the intradermal fluid delivery device 100 may include one or more processors and one or more memory units. The memory unit(s) may store program(s) and/or data used by the processor(s) to perform different processes described herein.

The processor(s) of the device 100 may receive the measurements from the pressure sensors 230 and may compare the measurements. In some embodiments, when the measurements received from the two sensors 230 are not within a threshold of each other, the processor(s) of the device 100 may not start the fluid delivery mechanism even if the fluid delivery mechanism is triggered. When the evenness sensor measurements indicate that the device 100 is not evenly positioned on the skin, the processor(s) of the device 100 may provide an alert through the status light 130, with audible signals, and/or by sending one or more signals through a wireless interface to external electronic devices. In some embodiments, more than two evenly distributed pressure sensors may be included around the cavity of the microneedle array. The outputs of these sensors may be processed by the processor to determine whether the device is evenly placed on the skin in all directions. Examples of pressure sensors may include, without limitations, flat pressure sensors, piezo electric sensors, etc.

The intradermal fluid delivery device 100, in some embodiments, may include one or more sensors to measure the skin softness of a person before applying the microneedle array 110. The intradermal fluid delivery device 100 parameters, such as the delivery time may be adjusted based on the measured skin softness value. A skin softness sensor, in some embodiments, may measure the indentation made by a cavity 240 on the surface of a person's skin. For example, in some embodiments, the skin softness sensor may include a light source 241 and a light sensor 242. The light source 241 and a light sensor (or photo sensor) 242 may be located the interior wall(s), and on the opposite sides, of a cavity 240. In some embodiments, the cavity 240 may be in proximity of the microneedle array cavity 120. In other embodiments, the light source 241 and a light sensor (or photo sensor) 242 may be positioned inside the microneedle array cavity 120. These embodiments may not include the cavity 240.

The light source 241 may be a laser light, a light emitting diode (LED), etc., and may direct a light towards the light sensor 241. The light sensor 242 may measure the light received from the light source 241. The processor(s) of the intradermal fluid delivery device 100 may receive measurements (e.g., as voltage values) from the light sensor 242. When a person's skin presses against the cavity were the light source and the light sensor are located, the skin enters the cavity and blocks a portion of the light that is directed from the light source 241 towards the light sensor 242. The more skin enters the cavity, the more light from the light source 241 is blocked from reaching the light sensor 242. The processor(s) of the intradermal fluid delivery device 100 may receive the light measurements from the light sensor and may determine the skin softness as a function of the amount of the light of the light source 241 that is blocked by the skin.

Figure 3B:
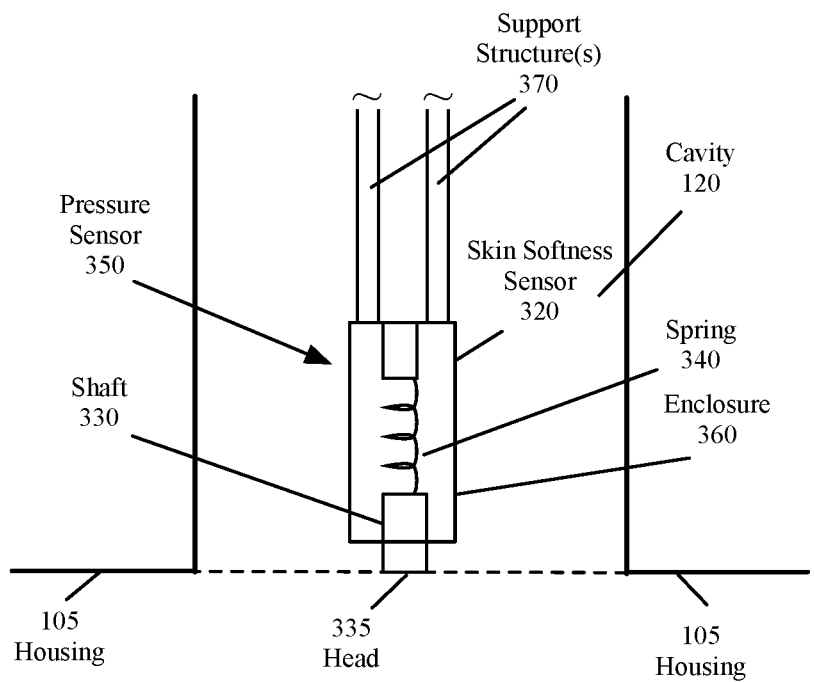
FIG. 3B is a front perspective view of a skin softness sensor located in the microneedle cavity of the intradermal fluid delivery device, according to various aspects of the present disclosure.

In some embodiments, the intradermal fluid delivery device 100, may include a skin softness sensor that includes a shaft and a spring. FIG. 3B is a front perspective view of a skin softness sensor with a shaft and a spring located in the microneedle cavity of the intradermal fluid delivery device, according to various aspects of the present disclosure. With reference to FIG. 3B, the skin softness sensor 320 and a portion of the housing 105 and a portion of the cavity 120 are shown. Other components of the intradermal fluid delivery device 100 are not shown for clarify.

The skin softness sensor 320 may include a shaft 330, a spring 340, and a pressure sensor 350. The skin softness sensor 320 may include an enclosure 360, which may be secured to the interior of the intradermal fluid delivery device 100 by one or more structures 370. The enclosure 360 may include an opening through which a portion of the shaft 330 may come out of the enclosure. The enclosure 360 may be positioned such that the head 335 of the shaft is substantially at the same level (as shown by the dashed line 305) as the housing 105.

When the intradermal fluid delivery device 100 is placed against a person's skin, the person's skin may press against the head 335 of the shaft 330, causing the shaft 330 to press against the spring 340. The pressure sensor 350 may measure the pressure applied by the spring 340. The processor(s) of the intradermal fluid delivery device 100 may receive the pressure measurements from the pressure sensor 370 and may determine the amount of displacement of the spring 340 based of the amount of change in the pressure measurement before and after the intradermal fluid delivery device 100 is placed on a person's skin. The processor(s) may determine the skin's softness as a function of the spring displacement (or as a function of the change in the pressure measurement before and after the device is placed on the skin).

Instead of the pressure sensor 350, some embodiments may include a potentiometer (not shown). A potentiometer is a measuring instrument that acts as a voltage divider for measuring voltage. The potentiometer is a three-terminal resistor that has a moving (e.g., sliding or rotating) contact that forms an adjustable voltage divider. When the spring 340 is displaced in response to the force applied by the head 335, the spring may move the potentiometers contact, resulting in a change of voltages of the voltage divider. The processor(s) may receive the voltage divider's voltages and may determine the skin's softness as a function of the change of the voltages of the voltage divider.

Instead of the pressure sensor 350 or a potentiometer, some embodiments may include a Hall effect sensor. A Hall effect sensor detects the presence and magnitude of a magnetic field and generates a voltage that is proportional to the strength of the magnetic field. In the embodiments that use a Hall effect sensor, the end of the shaft that is opposite to the head 335 may include a magnet and the Hall effect sensor may be positioned at the proximity of the magnet such that when the magnet moves, the distance between the magnet and the Hall effect sensor changes. As the shaft 335 moves, it pushes against the spring 340, the distance between the magnet at the end of the shaft 330 and the Hall effect sensor changes (e.g., the magnet gets closer to the Hall effect sensor), resulting in a change in the voltage generated by the Hall effect sensor. The processor(s) may receive the Hall effect sensor's voltage measurements and may determine the skin's softness as a function of the change of the Hall effect sensor's voltage measurements.

The microneedles 200 may be from a fraction of millimeter to several millimeters long in different embodiments. The microneedles 200, in some embodiments, may be configured to penetrate the outermost layer of a person's skin. The microneedles may include a hollow interior for delivering the fluid under the person's skin. The use of microneedle array to contact the skin to deliver the fluid provides minimal pinching feeling at the moment of the release of the microneedle array. The person receiving the fluid typically may feel no pain during the fluid delivery.

Figure 3C:
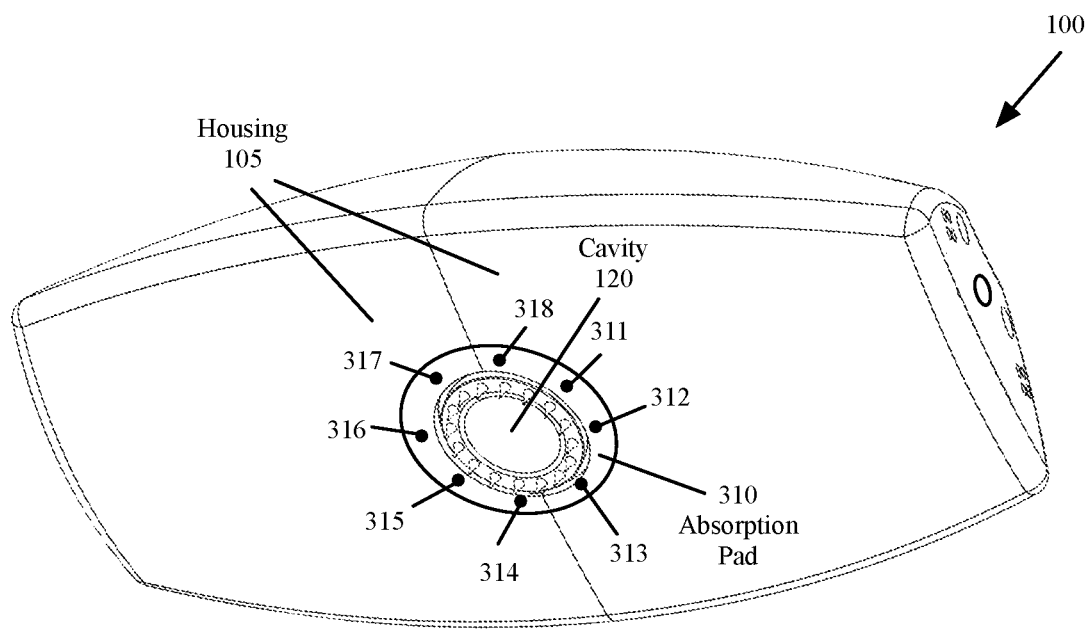
FIG. 3C illustrates a bottom perspective view of the intradermal fluid delivery device of FIG. 1 that includes an absorption pad, according to various aspects of the present disclosure.

The intradermal fluid delivery device 100, in some embodiments, may include an absorption pad around the perimeter of the microneedle array 110 to absorb any leaks that may occur during the fluid delivery. FIG. 3C illustrates a bottom perspective view of the intradermal fluid delivery device of FIG. 1 that includes an absorption pad, according to various aspects of the present disclosure.

With reference to FIG. 3C, the absorption pad 310 may be made of a fabric with fluid absorption effects. Examples of fabrics with absorption effects include, without limitations, cotton, silk, and flax. The absorption pad may be actively monitored during the fluid delivery to sense the leak. The processor(s) may generate an alarm that may be reported through the status light 130, by audio signals, and/or by sending one or more signals through a wireless interface to external electronic devices. A leak may be caused, for example, when the intradermal fluid delivery device 100 is not properly attached on the skin during the fluid delivery. For instance, the intradermal fluid delivery device 100 may be connected to the skin such that enough pressure is not made by the device to the skin, causing a leak.

Some embodiments may measure the impedance between one or more pairs of points on the absorption pad. For example, in the depicted embodiments, the impedance between the point pair 311-312, 313-314, 315-316, and 317-318 may be measured. When the absorption pad is dry, the impedance between each pair of points is very high. When there is a leak and the pad gets wet, the impedance between the two points in at least some of the pair of points drops. The processor(s) of the intradermal fluid delivery device 100 may compare the impedance between the two points with a threshold and may determine that the device is leaking when the impedance measurement is below the threshold. The absorption pad may also be passively monitored after the delivery to check for leaks by monitoring for the wetness or a change in the color of the absorption pad. In addition to, or in lieu of measuring the impedance, the absorption pad's fabric, in some embodiments, may be made of a hydrochromic material that changes color when the absorption pad gets wet.

In some of the present embodiments, the microneedle array 110 may be removed and may be replaced with an interface to an intravenous (IV) needle and to a custom IV bag. The device 100 may, therefore, be turned into a portable IV system that a patient may conveniently wear and be free to move around. This portable IV device may have all the features described herein and may include a wireless connection through which the device may be connected to other electronic devices for control or monitoring as needed in a point of care, in a hospital, or at home environment. The IV bag may be a special bag that is made out of many fluidic channels that keep the IV solution distributed across the bag such that the bag may be easily and comfortably wrapped around the arm of a person, or be worn on the body (e.g., on the shoulder), without pinching the fluid or blocking the fluid flow.

The intradermal fluid delivery device 100, in some embodiments, may include a near field communication (NFC) tag (not shown), a radio frequency identification (RFID) tag (not shown), and/or a bar code (not shown), such as, for example, and without limitations, a two-dimensional bar code, that may identify the fluid and/or the person receiving the fluid. In some embodiments, the NFC tag, the RFID tag, and/or the bar code may be programmed with the person's information before shipping. In these embodiments, a mobile device, such as a smartphone, may be used to connect to the device 100, read the information, and start the fluid or vaccine delivery process, after the device 100 is attached to the person's skin, based on the information.

In some embodiments, the NFC tag, the RFID tag, and/or the bar code may be used by an electronic device, such as a mobile device, to activate a link to connect, through a network, to a training video and/or training instruction on a website.

In some embodiments, the processor(s) of the intradermal fluid delivery device 100 may write, under password control, information regarding the fluid delivery (e.g., and without limitations, the identification of the person, the start and completion times of the fluid delivery, the location of the fluid delivery, the specific contents of the fluid, and/or the specific delivery program used to deliver the fluid to a person's skin to the NFC tag and/or the RFID tag. The information may be scanned and used if the intradermal fluid delivery device 100 is stored for future reference.

Figure 4:
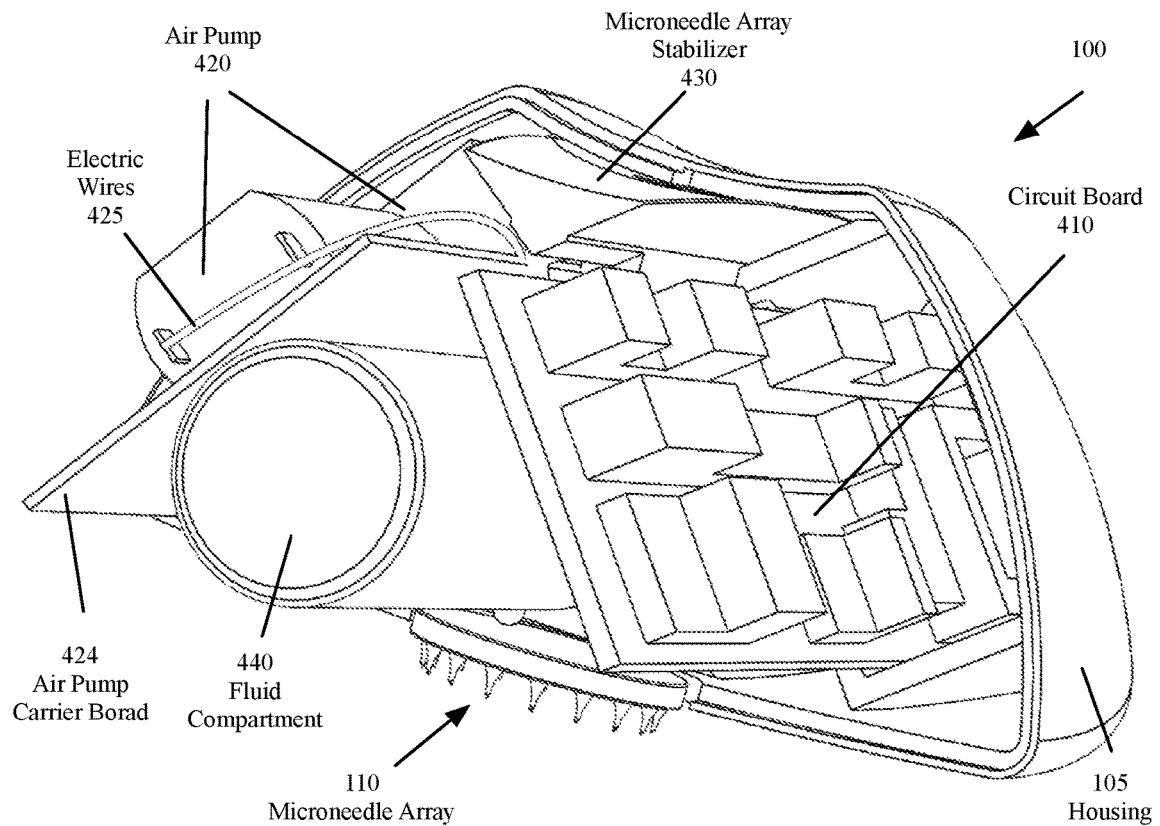
FIGS. 4 and 5 illustrate side perspective views of the intradermal fluid delivery device FIG. 1 with a portion of the housing removed, according to various aspects of the present disclosure.
Figure 5:
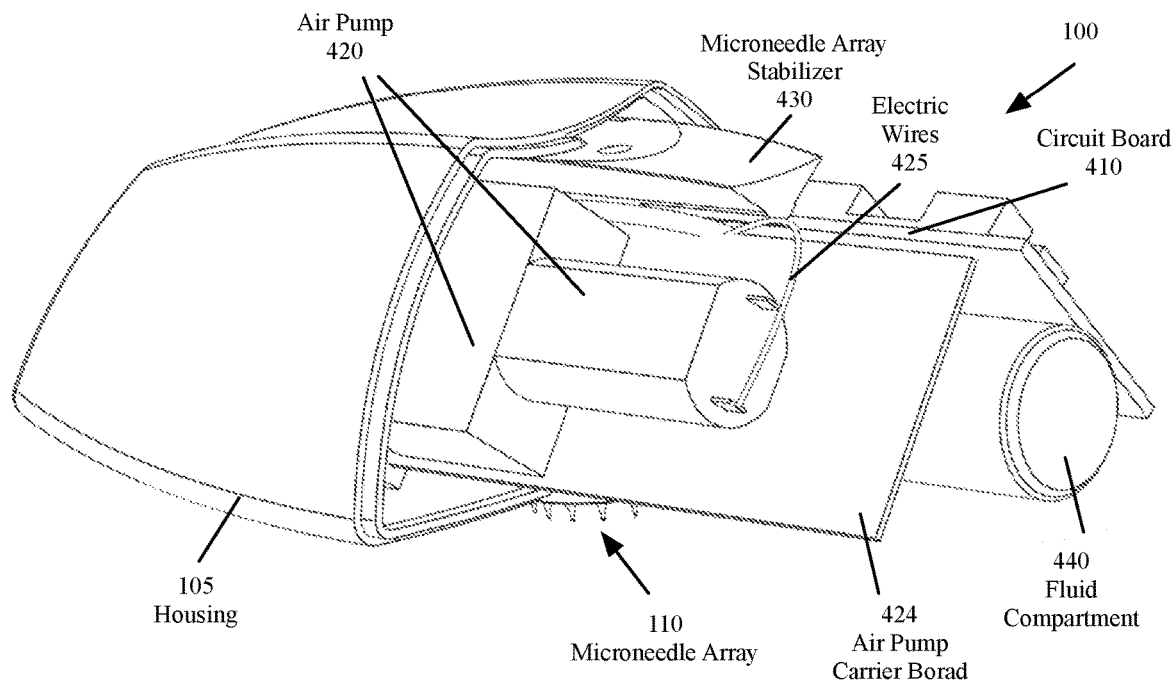
Figure 6:
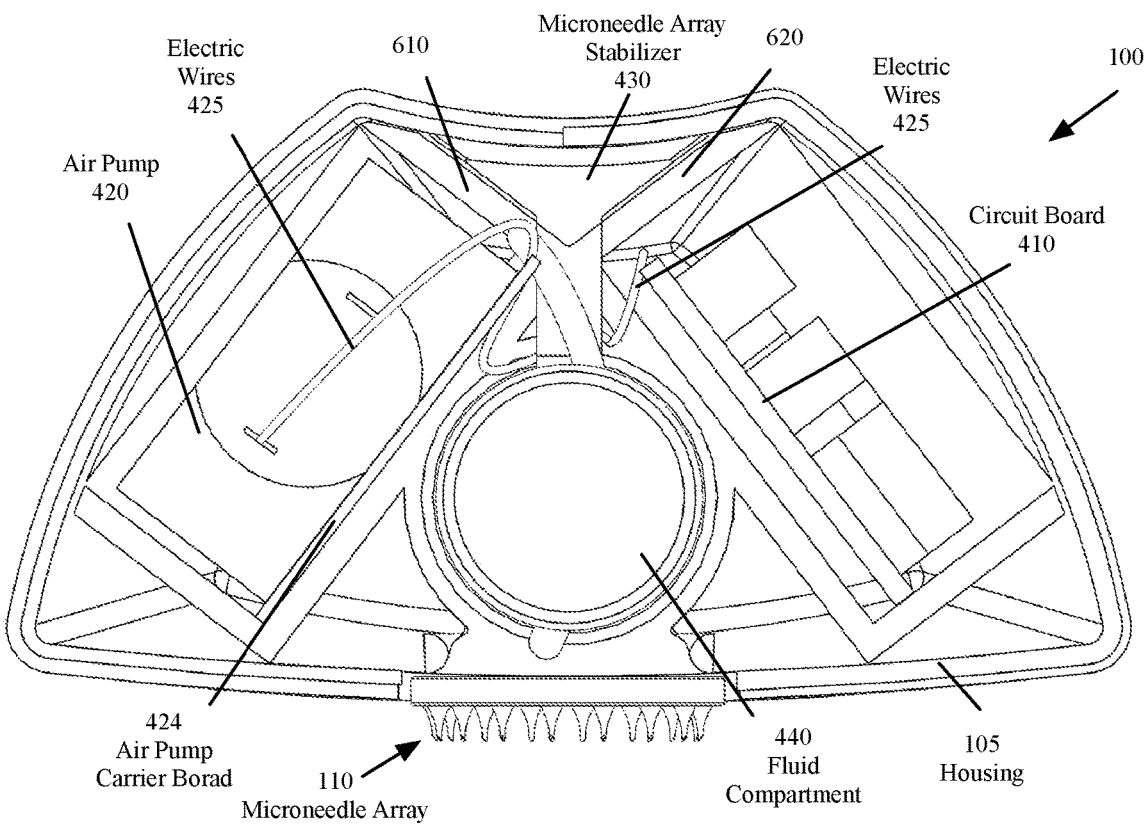
FIGS. 6 and 7, respectively, illustrate front and back elevation views of the intradermal fluid delivery device FIG. 1 with a portion of the housing removed, according to various aspects of the present disclosure.
Figure 7:
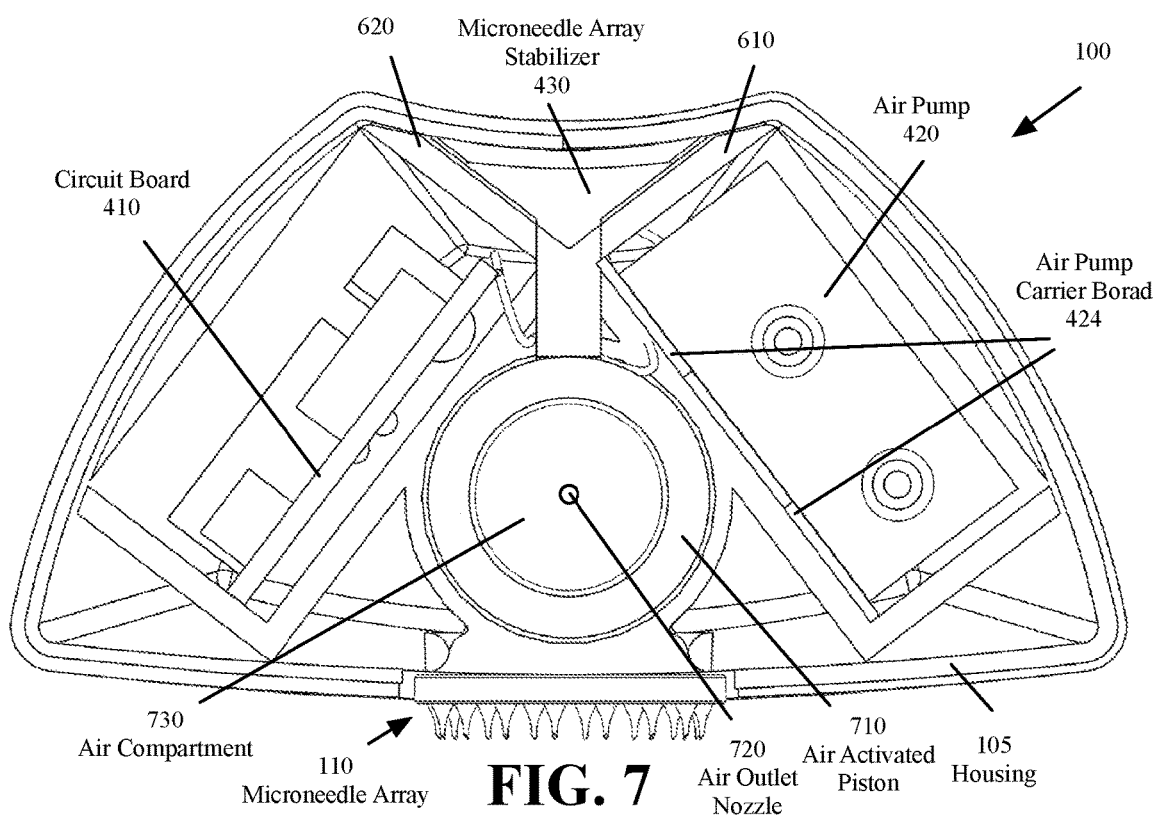

FIGS. 4 and 5 illustrate side perspective views of the intradermal fluid delivery device FIG. 1, with a portion of the housing removed, according to various aspects of the present disclosure. FIGS. 6 and 7, respectively, illustrate front and back elevation views of the intradermal fluid delivery device FIG. 1, with a portion of the housing removed, according to various aspects of the present disclosure.

With reference to FIGS. 4-7, the intradermal fluid delivery device 100 may include one or more circuit boards 410, an air pump 420, a microneedle array stabilizer 430, a fluid compartment 440, and an air activated piston 710 (FIG. 7). The circuit board(s) 410 may be, for example, and without limitations, printed circuit boards (PCBs). The circuit board(s) 410 may include electrical components such as, for example, and without limitations, one or more processors, one or more memory units, one or more batteries, etc. The circuit board(s) 410, in different embodiments, may include components such as a global positioning system (GPS) receiver, wireless transceivers such as Bluetooth transceiver and/or Wi-Fi transceiver, temperature sensors such as thermocouples and/or thermistors, etc. The processor(s) may be microcontrollers, microprocessors, etc., that may control the air pump 420 to provide a programmable fluid delivery time. The memory unit(s) may store program(s) and/or data used by the processor(s). The one or more batteries may provide power to the electronic components of device 100.

The wireless transceiver(s) may be used to connect the device 100 to one or more external electronic devices to send and receive data, to program the device 100, etc. The external electronic devices, in some embodiments, may use an application program that may be used to interface the external electronic devices with the device 100. The external electronic devices may be, for example, and without limitations, smartphones, tablet, computers, servers, etc.

A GPS receiver integrated in the device 100 and/or a GPS receiver on a mobile device that is wirelessly connected to the device 100 may provide the information about the location where the fluid delivery (e.g., vaccination) has occurred and may sent the information to a central data base that is available only to authorities such as the center for disease control (CDC). The person using the fluid may voluntarily opt in for providing additional information regarding the person.

The air pump 420 may be a micro air pump. As described below, the air pump 420 may be controlled by the processor(s) to move the air activated piston 710 to puncture the fluid compartment 440 to deliver the fluid through the microneedle array 100. The air pump 420 may move the air activated piston 710 by pumping air through the air outlet nozzle 720 into a closed air compartment 730 (FIG. 7 shows a cross section of the closed air compartment 730).

The processor(s), in some embodiments, may activate and deactivate the air pump 420 (e.g., by sending a series of on and off signals to the air pump) to control the delivery time of the fluid and/or to provide delays to allow the fluid to be smoothly absorbed through the skin. The air pump 420 may receive power from the battery/batteries on the circuit board 410 through one or more electric wires 425. The air pump 420 may be secured on a carrier board 424 for stability.

The microneedle stabilizer 430 is a fixed structure that may be used to stabilize the microneedle array 110. As shown in FIGS. 6-7, the microneedle stabilizer 410 may be attached to the sides 610 and 620 of the spaces that hold the air pump 420 and the circuit board(s) 410, respectively.

Figure 8:
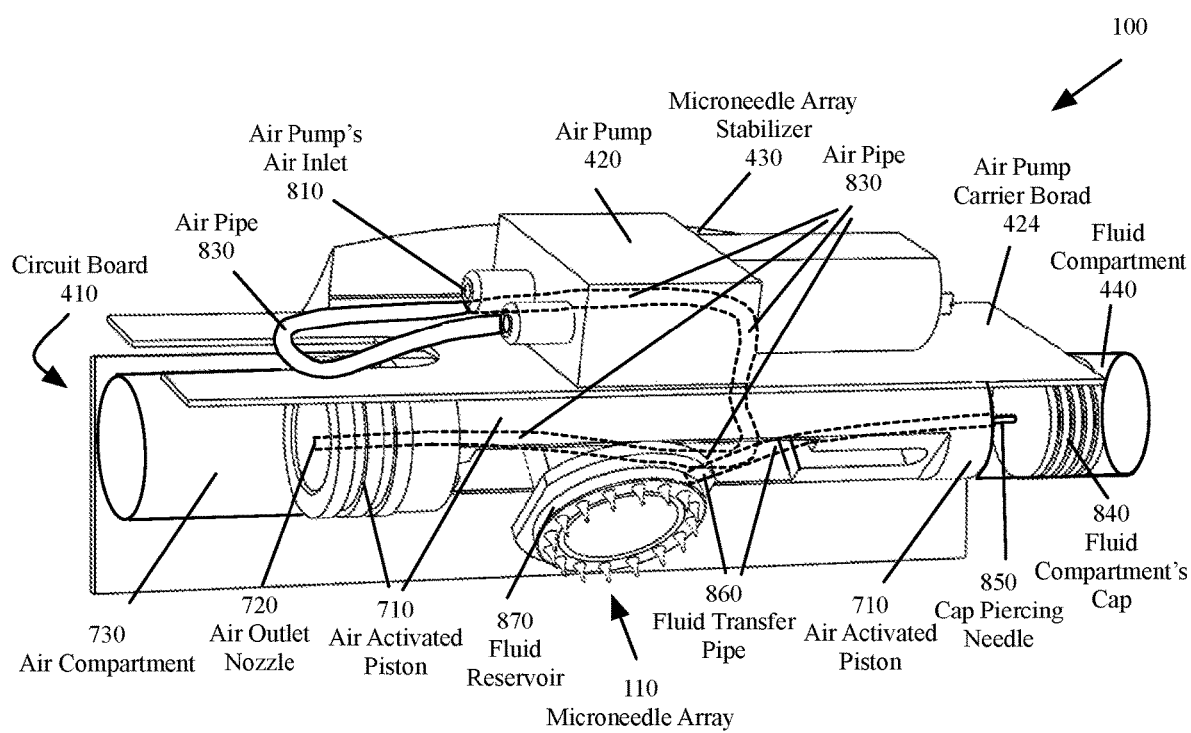
FIG. 8 is a bottom and side perspective view of a portion of the intradermal fluid delivery device of FIG. 1 with the housing removed, according to various embodiments of the present disclosure.

FIG. 8 is a bottom and side perspective view of a portion of the intradermal fluid delivery device 100 of FIG. 1, with the housing removed, according to various embodiments of the present disclosure. With reference to FIG. 8, the fluid delivery time of the intradermal fluid delivery device 100 may be programmable. The processor(s) may be configured to control the time required to administer the fluid to a person.

When the processor(s) receive one or more signals to start administering the fluid (the signal(s) may, e.g., be received through the activation switch 125 and/or wirelessly from an electronic device external to the device 100), the processor(s) may activate the air pump 420. The air pump 420 may take air in through the air pump's air inlet 810 and may pump air through the air pipe 830 and the air outlet nozzle 720 into the closed air compartment 730.

As the pressure in the closed air compartment 730 increases, the air activated piston 710 may start moving towards the fluid compartment 440 (e.g., in a left to right direction in the pictured orientation). As shown, the piston 710 may be connected to a cap piercing needle 850. As the air activated piston 710 moves in the direction of the fluid compartment, the cap piercing needle 850 may pierce the fluid compartment's cap 840, which may be made of a pierceable material such as, for example, and without limitations, rubber, silicone, etc.

The cap piercing needle 850 may be connected to a fluid transfer pipe 860. The cap piercing needle 850 and the fluid transfer pipe 860 may be configured such that the fluid from the fluid compartment 440 enters the fluid transfer pipe 860 from the point that the piercing needle 850 pierces the fluid compartment's cap 840. The fluid compartment's cap 840 may be configured to be movable. As the air activated piston 710 moves further in the direction of the fluid compartment 440, the fluid compartment's cap 840 pushes the fluid from the fluid compartment 440 into the fluid transfer pipe 860. The fluid transfer pipe 860 may transfer the fluid into a fluid reservoir 870 and may push the fluid, from the fluid reservoir 870, through the microneedle array 110 into the skin of the person wearing the intradermal fluid delivery device 100. The fluid reservoir 870 is an optional reservoir that some embodiments use to evenly distribute the fluid to individual needles of the microneedle array 110.

In some embodiments, the processor(s) may be configured to repeatedly turn the air pump 420 on or off (refereed herein as the controlled mode, or pulse mode, delivery of the fluid) in order for the fluid to gradually be transferred from the fluid compartment 440, through the microneedle array 110, into the person's skin. The processor(s) may be configured not only to control the total fluid delivery time but also the granularity of the fluid delivery. In other words, the total fluid delivery time may be set to T, and the time period T may be divided into smaller periods $t_1$ to $t_n$, where the fluid may be administered in a period t1, the fluid delivery may then be stopped for a period t2, followed by another fluid delivery period, etc. The periods t1 to tn may be the same or of different lengths. The processor, in some embodiments, may be configured to control the fluid delivery rate (e.g., the volume per second rate of the fluid delivery) for each individual fluid delivery period.

The prior art intradermal fluid delivery devices use a mechanical activation mechanism to deliver the fluid. The prior art intradermal fluid delivery devices include an activation button. When the activation button is pushed, a spring is released, and the fluid is pushed from a reservoir into a pipe that is connected to a microneedle array. The fluid is delivered through the microneedle array with no control.

The controlled mode delivery of the present embodiments allows for the flexibility of the step-by-step delivery of vaccines and other type of fluids and liquids and provides the technical advantage of allowing the skin to absorb a very small dose (e.g., a micro-dose) of the fluid before delivering the next micro-dose. Each vaccine or fluid may have its own delivery duration and delivery rate requirements, which may be programmed into the intradermal fluid delivery device 100 of the present embodiments. The programming may be done at the manufacture time, at the shipment time, or in the field using an application program running on an external electronic device that is wirelessly connected to the intradermal fluid delivery device 100. The application program may provide a user interface with options to program the total duration of the fluid delivery, the number of fluid delivery and fluid stoppage periods, and the duration of each individual fluid delivery and fluid stoppage period. The programming provides control over the total duration of fluid delivery and the fluid delivery rate. The delivery rate may be programmed to stay constant by selecting the same amount of time for all fluid delivery periods and the same amount of time for all fluid stoppage periods. Alternatively, each fluid delivery period and each fluid stoppage period may individually be programmed.

Some embodiments may include three activation buttons (not shown), where each activation button may be preprogrammed to provide a particular delivery rate and/or a particular set of values of the above-mentioned $t_1$ to $t_n$ periods. As a non-limiting example, some embodiments may provide three activation buttons for slow, medium, and fast rates of delivery.

Some embodiments may use an actuator (e.g., a linear actuator comprising a motor, a gear box, and a shaft), instead of the air pump 420 and the air pipe 830, to push or pull the piston 710. In these embodiments, the linear actuator may move the piston 710 and the cap piercing needle 850 to pierce the fluid compartment's cap 840 and to transfer the fluid from the fluid compartment 440 into the fluid transfer pipe 860 and the into microneedle array 110.

In some embodiment, a peristaltic pump may be used instead of the air pump 420, the air pipe 830, the air activated piston 710, and the air compartment 730 to draw fluid from the fluid compartment through the fluid transfer pipe 860 and push the fluid through the microneedle array 110. In these embodiments, a shaft or a piston connected to the peristaltic pump's motor may move the cap piercing needle 850 to pierce the fluid compartment's cap 840 and to transfer the fluid from the fluid compartment 440 into the fluid transfer pipe 860 and into the microneedle array 110.

In some of the present embodiments (with a pump and/or an actuator), the cap piercing needle 850 may be configured to pierce the fluid compartment's cap 840 when the fluid compartment 440 is inserted into the intradermal fluid delivery device 100 (e.g., through the fluid compartment insertion window 220 of FIG. 2). In these embodiments, a piston (or a shaft) may be used to move the fluid compartment's cap 840 to transfer the fluid from the fluid compartment 440 into the fluid transfer pipe 860 and into the microneedle array 110.

Figure 9:
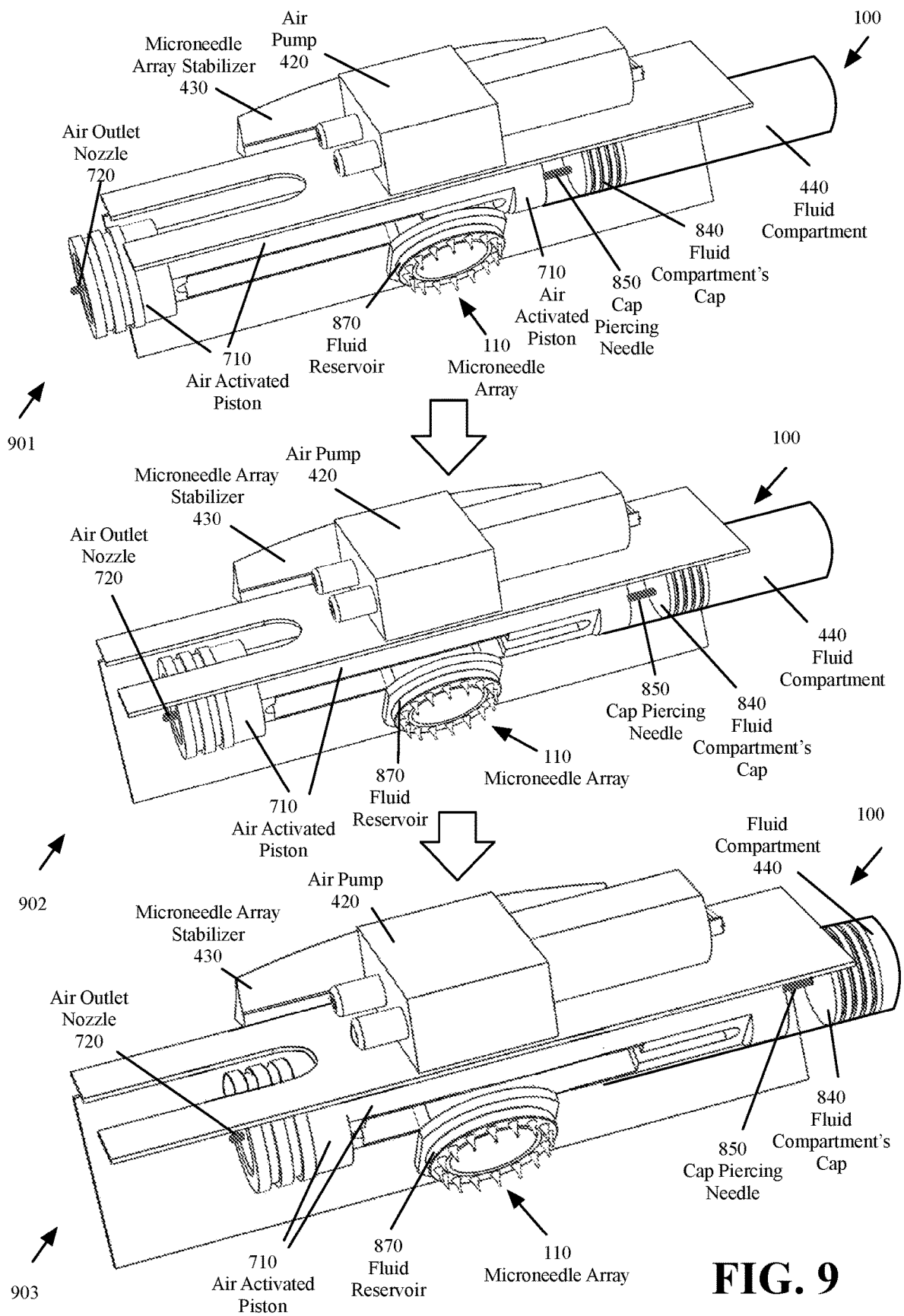
FIG. 9 is a bottom and side perspective of the intradermal fluid delivery device of FIG. 8 illustrating the air activated piston pushing the fluid compartment's cap to force the fluid out of the fluid compartment, according to various aspects of the present embodiments.

FIG. 9 is a bottom and side perspective of the intradermal fluid delivery device 100 of FIG. 8 illustrating the air activated piston pushing the fluid compartment's cap to force the fluid out of the fluid compartment, according to various aspects of the present embodiments. With reference to FIG. 8, some details, such as the air pipe 830, the fluid transfer pipe 860, and the air compartment 730 are not shown for clarity.

FIG. 9, as shown, includes three operational steps 901-903. In step 901, the cap piercing needle 850 has pierced the fluid compartment's cap 840, the microneedle array 110 is deployed, and the fluid is being transferred from the fluid compartment 440 into the fluid reservoir 870. The air pump 420 may be pushing air through the air outlet nozzle 720 into the closed air compartment 730 (FIG. 8). As described above, the processor(s) may be configured to either pulse the air pump 420 on/off or to keep the air pump continuously on to push the air activated piston 710 towards the fluid compartment 440. The fluid may be administered into the person's skin through the microneedle array 110.

In step 902, the air activated piston 710 has moved further towards the fluid compartment 440. As shown in this step, the fluid compartment 440 is being emptied as the fluid is administered through the microneedle array 110.

In step 903, the air activated piston 710 has emptied the fluid compartment 440. The device 100 may send a completion signal, for example through the status light 130, through one or more audible signals, and/or through a wireless interface to one or more external electronic devices. The processor(s) may stop the air pump 420 after the fluid delivery is completed.

Figure 10:
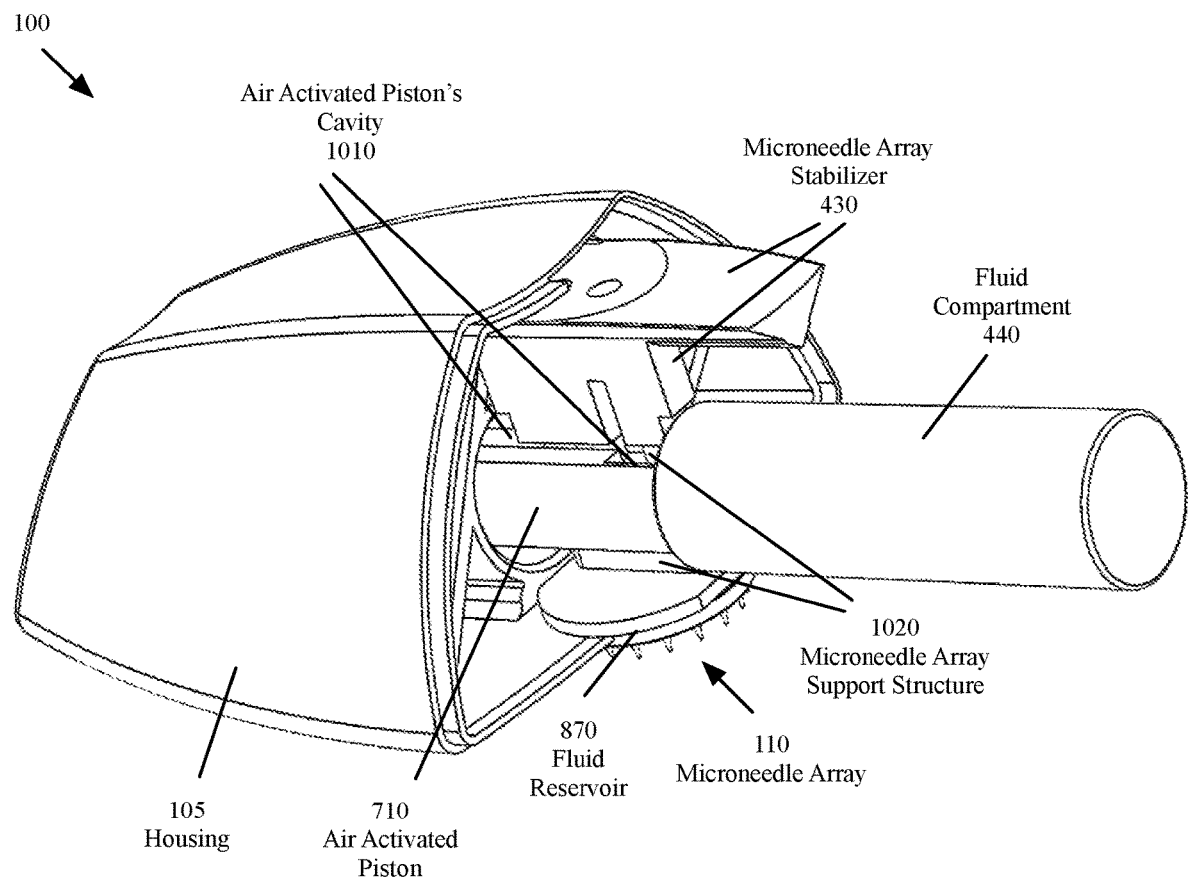
FIG. 10 is a side perspective view of the microneedle deployment portion of the intradermal fluid delivery device of FIG. 1, according to various aspects of the present embodiments.

FIG. 10 is a side perspective view of the microneedle deployment portion of the intradermal fluid delivery device of FIG. 1, according to various aspects of the present embodiments. With reference to FIG. 10, a section of the housing 105 is removed to show the details of the microneedle deployment mechanism of the intradermal fluid delivery device 100.

As shown, the microneedle array 110 may be attached to a microneedle array support structure 1020. As described above with reference to step 102 of FIG. 1, the microneedle array 110 may be inside a cavity 120 in the housing 105 prior to being deployed. The microneedle array support structure 1020 may be positioned inside a cavity 1010 in the air activated piston 710.

FIG. 11A is a side perspective view and FIG. 11B is a front perspective view of the microneedle array support structure 1020 of FIG. 10, according to various aspects of the present embodiments. FIG. 12 is a top perspective view of the air activated piston 710 of FIG. 10, according to various aspects of the present embodiments. With reference to FIGS. 11A, 11B, and 12, the microneedle array support structure 1020 may include a shaft 1110, one or more poles 1120 (in this example, three poles), and two tabs 1130.

The shaft 1110 may hold the fluid reservoir 870 and the microneedle array 110. The poles 1120 may hold the microneedle array support structure 1020 against the microneedle array stabilizer 430 (as described below with reference to FIG. 13). The microneedle array support structure 1020 may include springs (as described below with reference to FIG. 13) that apply pressure on the poles 1120. Prior to the deployment of the microneedle array 110, the tabs 1130 may rest on the two flat support surfaces 1210 of the air activated piston 710. The tabs 1130 and the support surfaces 1210 may, therefore, prevent the microneedle array support structure 1020 and the attached microneedle array 110 to move. As described below with reference to FIG. 14, once the air activated piston 710 moves towards the fluid compartment, the support surfaces 1210 move away from under the tabs 1130, causing the microneedle array 110 to be deployed.

Figure 13:
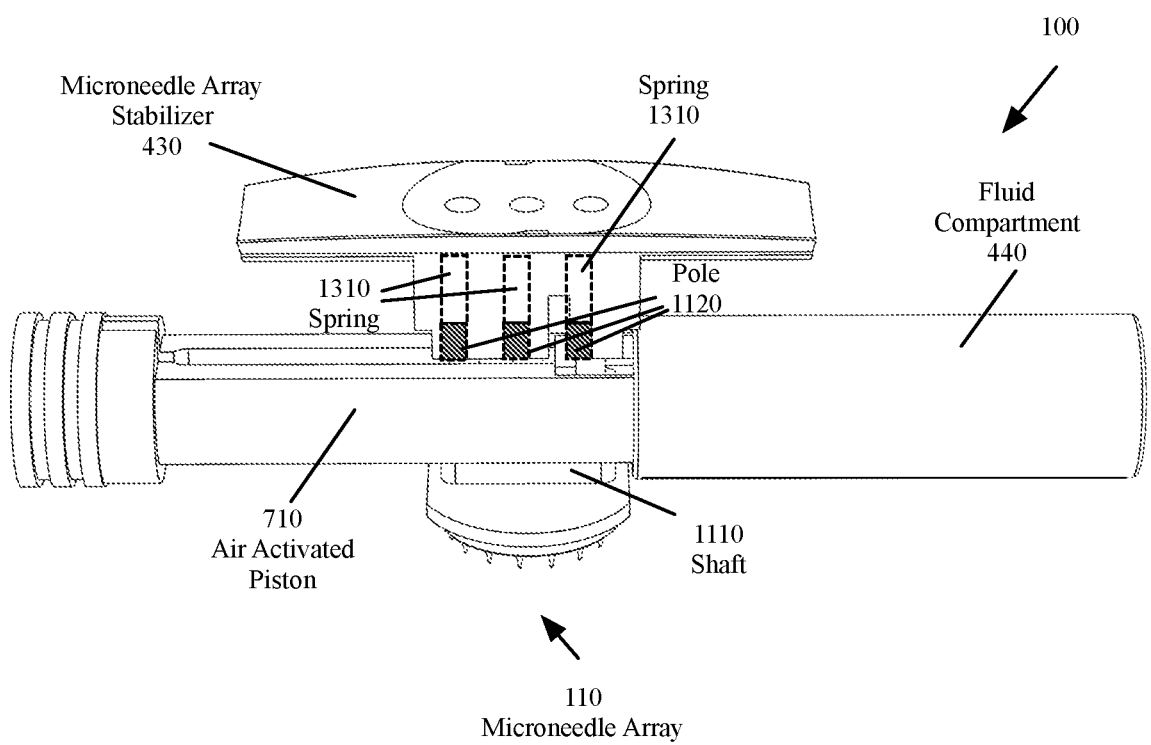
FIG. 13 is a side perspective view of the air activated piston and the microneedle array stabilizer of FIG. 10, according to various aspects of the present embodiments.

FIG. 13 is a side perspective view of the air activated piston and the microneedle array stabilizer of FIG. 10, according to various aspects of the present embodiments. With reference to FIG. 13, the poles 1120 may be positioned inside hollow cavities of the microneedle array stabilizer 430 that may prevent the microneedle array 110 from moving prior to the deployment.

The microneedle array stabilizer 430 may include the springs 1310 that may apply pressure to the poles 1120. As described below with reference to FIG. 14, as long as the tabs 1130 are positioned on the support surfaces 1210, the shaft 1110 and the microneedle array 110 do not move towards the bottom of the device's housing and do not come into contact with the skin of the person who is wearing the device 100.

Figure 14:
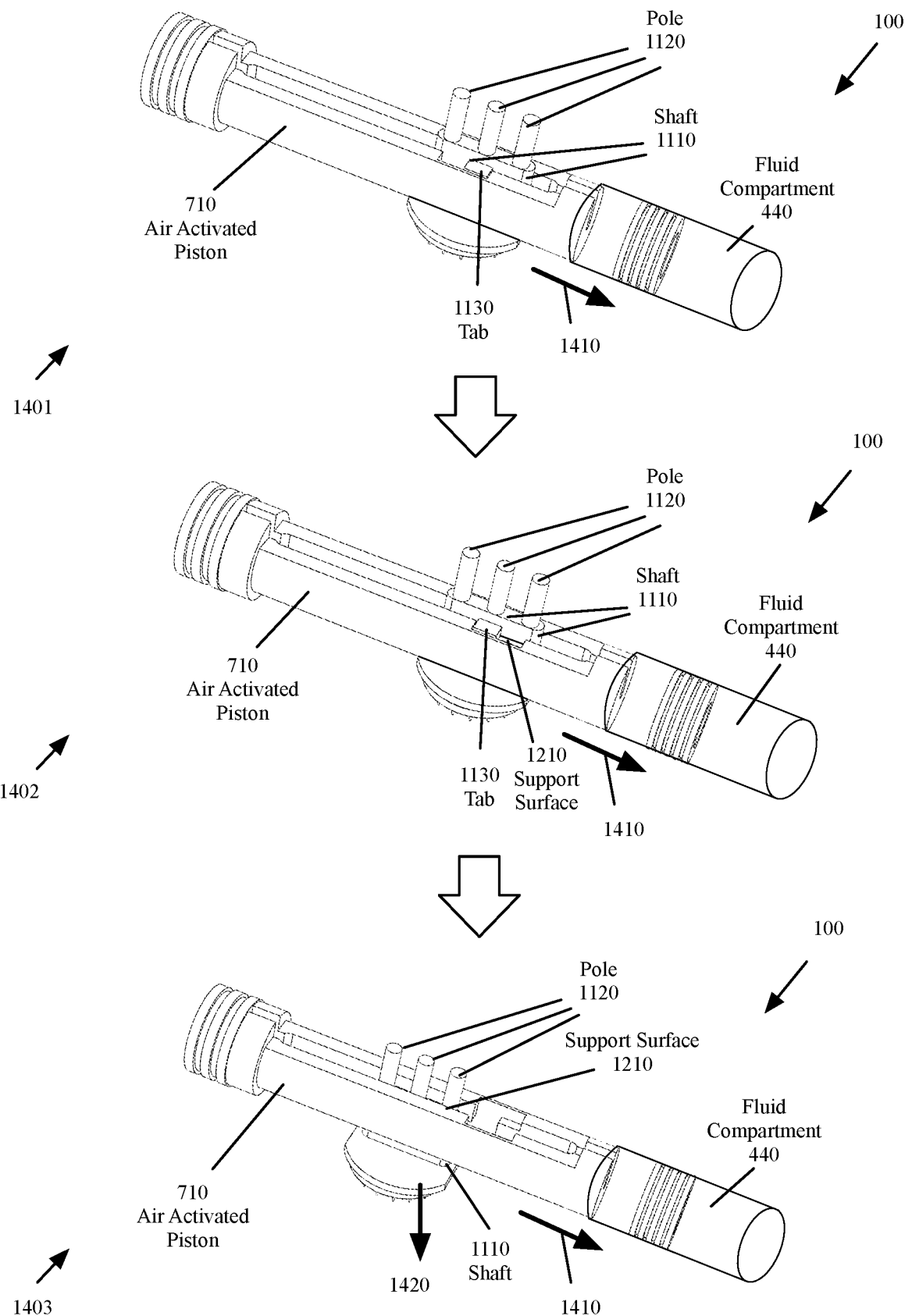
FIG. 14 is a top perspective view of a portion of the intradermal fluid delivery device of FIG. 10 illustrating an example deployment of the microneedle array, according to various aspects of the present disclosure.

FIG. 14 is a top perspective view of a portion of the intradermal fluid delivery device of FIG. 10, illustrating an example deployment of the microneedle array, according to various aspects of the present disclosure. With reference to FIG. 14, a section of the housing 105 is removed to show the details of the microneedle deployment mechanism of the intradermal fluid delivery device 100.

FIG. 14, as shown, includes three operational steps 1401-1403. In step 1401, the tabs 1130 (in the perspective view of FIG. 14, only one tab 1130 is shown) may be resting on the support surfaces 1210 (not visible in step 1401). As the air pump 420 pumps air in the air compartment 730 (as described above with reference to FIG. 8), the air activated piston 710 moves towards the fluid compartment 440 (in the direction of the arrow 1410) and the support surfaces 1210 move from under the tabs 1130.

In step 1402, the air activated piston 710 has moved further towards the fluid compartment 440 and the support surfaces 1210 have move from under the tabs 1130 (a portion of one of the support surfaces 1210 is visible in step 1402). Once the support surfaces 1210 are no longer underneath the tabs, the springs 1310 (FIG. 13) in the microneedle array stabilizer 420 apply pressure to the poles 1120 and the shaft 1110 and the attached microneedle array may move down (in step 1403) towards the bottom of the housing 105 and may penetrate the skin of the person who is wearing the device 100.

Figure 15:
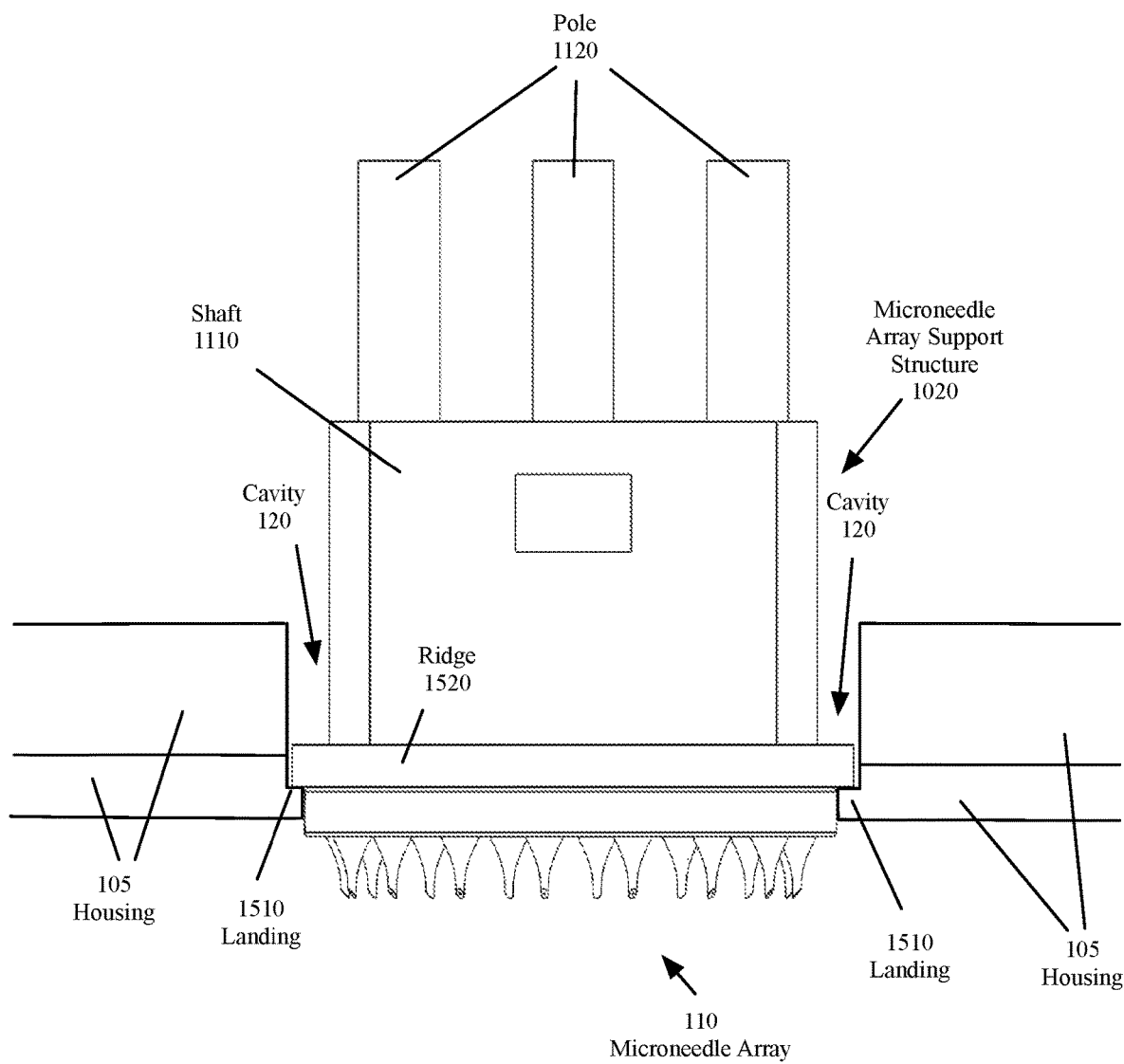
FIG. 15 is a front perspective view of a portion of the microneedle array support structure, according to various aspects of the present embodiments.

FIG. 15 is a front perspective view of a portion of the microneedle array support structure, according to various aspects of the present embodiments. As shown, the device's housing 105 may including one or more landing edges 1510 and the microneedle array support structure 1020 may include a ridge 1520 at the end of the shaft 1110.

The landing edge(s)1510 and the ridge 1520 may be configured such that the microneedle array 110 may not move out of the housing's cavity 120 for more than a predetermined distance (e.g., a fraction of millimeter to several millimeters, depending on the configuration). The landing edge(s) 1510 and the ridge 1520 may, therefore, prevent the microneedle array 110 to penetrate more than a predetermined distance into a person's skin and may also prevent the microneedle array 110 to shoot out of the housing 105 if the microneedle array 110 is accidentally deployed without the device 100 being worn by a person.

The intradermal fluid delivery device 100, in some embodiments, may optionally include a small speaker and/or several small LEDs (e.g., similar to singing birthday cards) to play music and create fun lighting patterns when the delivery is done or during the delivery. This option may be useful for using the device on small children and adding an entertainment element to distract them from the fear of getting a vaccine or fluid shot and making it more fun for them. The children would probably want to keep the device and brag to their friends about being vaccinated.

The device may be placed on a child's arm but not immediately activated. The device may then be activated through an application on a wirelessly connected external electronic device by, for example, a parent when the child is distracted and not in a panic or unhappy mood. Some embodiments may provide an activation switch (not shown), which is different than the activation switch 125 (FIG. 1), to start playing musical notes and/or to start the light patterns.

The intradermal fluid delivery device 100, in some embodiments, may be wirelessly connected to one or more external devices. In these embodiments, the fluid delivery may be started when the processor(s) of the intradermal fluid delivery device 100 receive one or more activation signals from an external electronic device. In some of these embodiments, the processor(s) may receive one or more signals to start playing music and/or to start the light patterns. The signal(s) to start the fluid delivery may be different than the signal(s) to start playing music and/or to start the light patterns.

The intradermal fluid delivery device of the present embodiments is a low-cost device ideal for mass deployment. For example, when the coronavirus disease 2019

(COVID-19) vaccine became ready for use, hundreds of millions of people across the globe need to be vaccinated in as short a period of time as possible. Having them lined up at clinics or even mobile units is a slow process and takes a very long time. With some preparedness ahead of time, the vaccine delivery device of the present embodiments may be shipped to everyone during a pandemic. Delivery services such as United State Postal Service (USPS), United Parcel Service (UPS), Amazon, Federal Express (FedEx), Uber, Lift, and many other services may get the device to millions of people in a few days.

Figure 16:
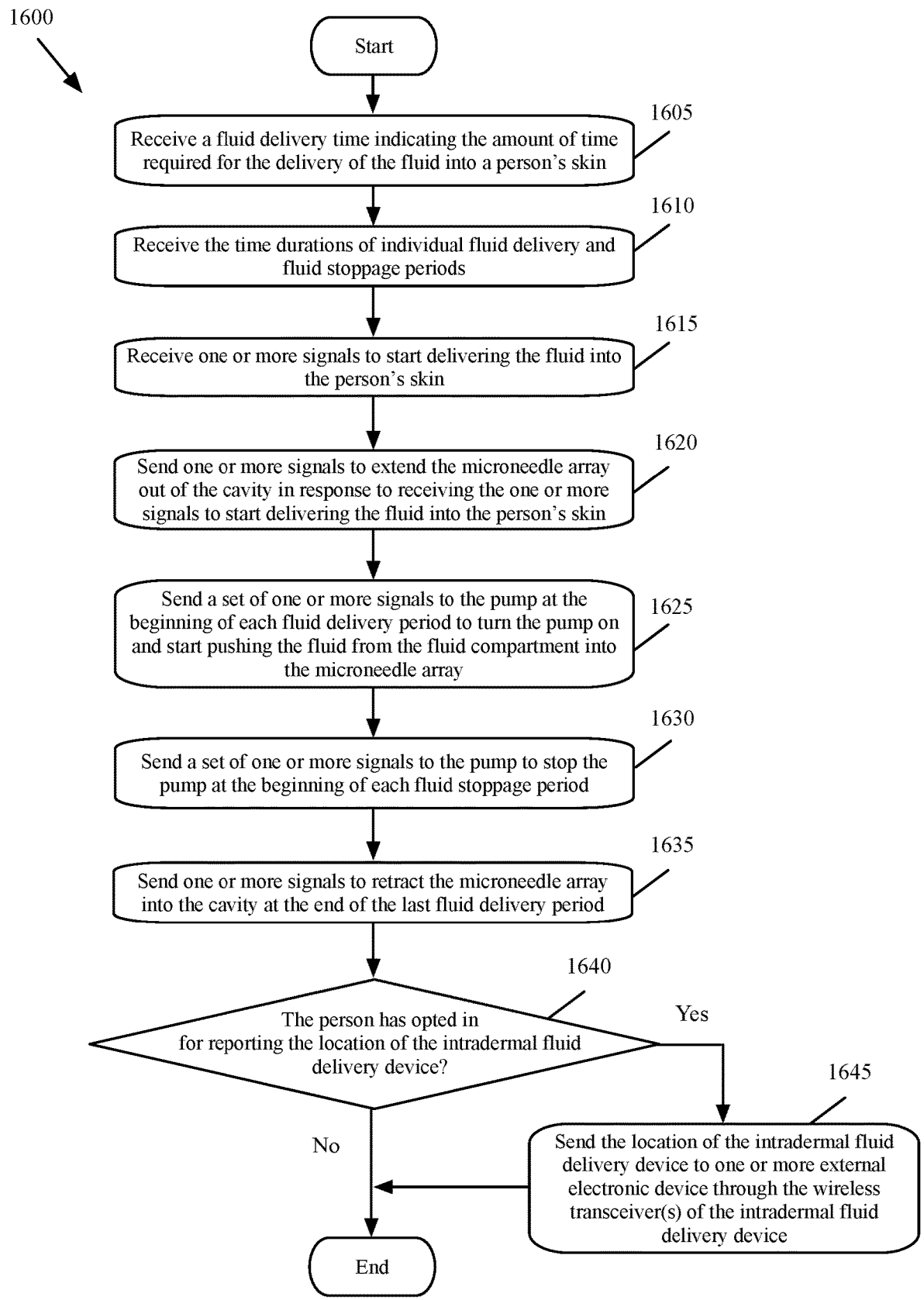
FIG. 16 is a flowchart illustrating an example process for delivering fluid into a person's skin by the intradermal fluid delivery device, according to various aspects of the present disclosure.

FIG. 16 is a flowchart illustrating an example process 1600 for delivering fluid into a person's skin by the intradermal fluid delivery device, according to various aspects of the present disclosure. In some of the present embodiments, the process 1600 may be performed by a processor of the intradermal fluid delivery device.

With reference to FIG. 16, a fluid delivery time indicating the amount of time required for the delivery of the fluid into a person's skin may be received (at block 1605). As described above with reference to FIGS. 2 and 3B, the skin softness of the person, in some embodiments, may be determined and the fluid delivery time may be adjusted based on the softness of the person's skin.

The time durations of individual fluid delivery and fluid stoppage periods may be received (at block 1610). For example, at least some of the individual fluid delivery periods may be the different from each other, at least some of the individual fluid stoppage periods may be the different from each other, all of the individual fluid delivery periods may be the same, all of the individual fluid stoppage periods may be the same, there may be only one fluid delivery period, and/or there may be only one fluid stoppage period.

At block 1615, one or more signals may be received to start delivering the fluid into the person's skin. For example, the one or more signals to start delivering the fluid into the person's skin may be received from an external electronic device that is communicatively coupled to the processor thorough the wireless transceiver of the intradermal fluid delivery device. The one or more signals to start delivering the fluid into the person's skin may be received from a set of one or more activation buttons of the intradermal fluid delivery device.

Next, one or more signals may be sent (at block 1620) to extend the microneedle array out of the cavity in response to receiving the one or more signals to start delivering the fluid into the person's skin. As described above with reference to FIG. 2, the evenness of the intradermal fluid delivery device 120 of the person's skin may be determined, in some embodiments, and the microneedle array may be extended out of the cavity in response only after the intradermal fluid delivery device 120 is to be positioned evenly on the person's skin.

Furthermore, as described above with reference to FIGS. 8 and 9, the air pump may be configured to pump air into the closed air compartment causing the piercing needle on the air activated piston to pierce a hole into the fluid compartment through which the fluid is moved into the fluid transfer pipe and into the microneedle array.

At block 1625, a set of one or more signals may be sent to the pump at the beginning of each fluid delivery period to turn the pump on and start pushing the fluid from the fluid compartment into the microneedle array. A set of one or more signals may be sent (at block 1630) to the pump to stop the pump at the beginning of each fluid stoppage period. One or more signals may be sent (at block 1635) to retract the microneedle array into the cavity at the end of the last fluid delivery period.

Next, a determination may be made (at block 1640) whether the person has opted in for reporting the location of the intradermal fluid delivery device. If not, the process 1600 may end. Otherwise, the location of the intradermal delivery device may be sent (at block 1645) to one or more external electronic devices through the wireless transceiver(s) of the intradermal delivery device. The process 1600 may then end.

The specific operations of the process 1600 may not be performed in the exact order shown and described. Furthermore, the specific operations described with reference to FIG. 16 may not be performed in one continuous series of operations in some embodiments, and different specific operations may be performed in different embodiments. For example, in some aspects of the present embodiments, the process 1600 may not report the location of the intradermal fluid delivery device. In these embodiments, the blocks 1640 and 1645 may be skipped.

As another example, one or more signals may be received to play music and/or to play a light pattern, for example, to distract a child before, during, or after the fluid delivery. In these embodiments, in response to receiving the one or more signals, a set of musical notes may be played and/or a plurality of light sources may be turned on and off to create a set of lighting patterns.

Furthermore, as described above with reference to FIG. 3C, a voltage may be applied between a pair of points on an absorption pad that is positioned around the microneedle array cavity. The electric current between the pair of points may be measured after the voltage is applied. The absorption pad may then be determined to be wet based on the electric current. For example, when the absorption pad between the pair of points is dry, the electric current between the pair of points is less than or equal to a threshold, and when the absorption pad between the pair of points is wet, the electric current between the pair of points is larger than the threshold. One or more signals may be generated when the absorption pad is determined to be wet.

The electronic devices such as the intradermal fluid delivery device of the present embodiments, the electronic devices, the client devices, and/or the servers described above may include memory. The memory in the above examples may be one or more units of similar or different memories. For example, the electronic devices' memory may include, without any limitations, random access memory (RAM), read-only-memory (ROM), read-only compact discs (CD-ROM), erasable programmable read-only memories (EPROMs), electrically erasable programmable read-only memories (EEPROMs), flash memory (e.g., secured digital (SD) cards, mini-SD cards, micro-SD cards, etc.), magnetic and/or solid state hard drives, ultra-density optical discs, and/or any other optical or magnetic media.

Electronic devices described above may include one or more processing units. The processing unit may be a single-core processor or a multi-core processor in different embodiments. The electronic devices in some of the present embodiments may store computer program instructions in the memory, which may be a machine-readable or computer-readable medium (alternatively referred to as computer-readable storage medium, machine-readable medium, or machine-readable storage medium). The computer-readable medium may store a program that is executable by at least one processing unit and includes sets of instructions for performing various operations. Examples of programs or computer code include machine code, such as is produced by a compiler, and files including higher-level code that are executed by a computer, an electronic component, or a microprocessor using an interpreter. From these various memory units, the processing unit may retrieve instructions to execute and data to process in order to execute the processes of the present embodiments.

As used in this disclosure and any claims of this disclosure, the terms such as "processing unit," "processor," "controller," "microcontroller," "server", and "memory" all refer to electronic or other technological devices. These terms exclude people or groups of people. For the purposes of this disclosure, the terms display or displaying means displaying on an electronic device. As used in this disclosure and any claims of this disclosure, the terms "computer readable medium," "computer readable media," and "machine readable medium" are entirely restricted to tangible, physical objects that store information in a form that is readable by a processing unit. These terms exclude any wireless signals, wired download signals, and any other ephemeral or transitory signals.

In a first aspect, an intradermal fluid delivery device comprises: a housing; a fluid compartment configured to hold a quantity of fluid; a microneedle array configured to deliver the fluid into a person's skin, the microneedle array positioned in a cavity of the housing; an air pump configured to push the fluid out of the fluid compartment and into the microneedle array; a processor configured to: receive a fluid delivery time indicating an amount of time required for the delivery of the fluid into the person's skin, wherein the fluid delivery time comprises a plurality of fluid delivery periods and a plurality of fluid stoppage periods, wherein each fluid delivery period is followed by a fluid stoppage period, and wherein durations of at least two fluid delivery periods in the plurality of fluid delivery periods are different from each other; receive one or more signals to start delivering the fluid into the person's skin; send one or more signals to extend the microneedle array out of the cavity in response to receiving the one or more signals to start delivering the fluid into the person's skin; send a set of one or more signals to the air pump at a beginning of each fluid delivery period to turn the air pump on and start pushing the fluid from the fluid compartment into the microneedle array; send a set of one or more signals to the air pump to stop the air pump at a beginning of each fluid stoppage period; and send one or more signals to retract the microneedle array into the cavity at an end of a last fluid delivery period in the plurality of fluid delivery periods.

In an embodiment of the first aspect, durations of at least two fluid stoppage periods in the plurality of fluid stoppage periods are different from each other.

An embodiment of the first aspect further comprises: a wireless transceiver, wherein the processor is configured to: receive the one or more signals to start delivering the fluid into the person's skin from an external electronic device that is communicatively coupled to the processor thorough the wireless transceiver.

Another embodiment of the first aspect further comprises: a set of one or more activation buttons, wherein the processor is configured to: receive the one or more signals to start delivering the fluid into the person's skin when one of the activation buttons in the set of activation buttons is depressed.

Another embodiment of the first aspect further comprises: a wireless transceiver, where in the processor is configured to: determine, after the end of the last fluid delivery period in the plurality of fluid delivery periods, whether the person has opted in for reporting a location of the intradermal delivery device; send a location of the intradermal delivery device to one or more external electronic device through the wireless transceiver when the person is determined to have opted in for the reporting.

In another embodiment of the first aspect, the cavity is a first cavity, the intradermal delivery device further comprising: a second cavity in the housing; a light source and a light sensor positioned on opposite sides of an interior of the second cavity, wherein the light source is positioned to direct light to the light sensor, and wherein the light source and the light sensor are positioned such that when a person's skin enters the second cavity, at least a portion of the light directed from the light source to the light sensor is blocked by the skin; wherein the processor is configured to: receive light measurements from the light sensor; determine a softness of the person's skin as a function of the amount of the light source's light that is blocked by the skin; and adjust the fluid delivery time based on the softness of the person's skin.

Another embodiment of the first aspect further comprises: a light source and a light sensor positioned on opposite sides of an interior of the cavity where the microneedle array is positioned, wherein the light source is positioned to direct light to the light sensor, and wherein the light source and the light sensor are positioned such that when a person's skin enters the cavity, at least a portion of the light directed from the light source to the light sensor is blocked by the skin; wherein the processor is configured to: receive light measurements from the light sensor; determine a softness of the person's skin as a function of the amount of the light source's light that is blocked by the skin; and adjust the fluid delivery time based on the softness of the person's skin.

Another embodiment of the first aspect further comprises: a shaft; a spring connected to the spring; and a pressure sensor connected to the spring; wherein the spring and the pressure sensor are positioned inside the cavity where the microneedle array is positioned; wherein the shaft is positioned inside the cavity where the microneedle array such that a head of the shaft is substantially at a same level as an opening of the cavity; wherein when a person's skin enters the cavity, the skin applies a pressure on the shaft, causing the shaft to press the spring, causing the spring to apply a pressure to the pressure sensor; wherein the processor is configured to: receive pressure measurements from the pressure sensor; determine a softness of the person's skin as a function of the amount of the pressure applied by the spring to the pressure sensor; and adjust the fluid delivery time based on the softness of the person's skin.

Another embodiment of the first aspect further comprises: a shaft; a spring connected to the spring; and a potentiometer connected to the spring, wherein the potentiometer comprises a moving contact that is configured to move and change proportions of voltages of a voltage divider of the potentiometer; wherein the spring and the potentiometer are positioned inside the cavity where the microneedle array is positioned; wherein the shaft is posited inside the cavity such that a head of the shaft is substantially at a same level as an opening of the cavity; wherein when a person's skin enters the cavity, the skin applies a pressure on the shaft, causing the shaft to press the spring, causing the spring to potentiometer's contact to move and change the proportion of the voltages of the potentiometer; and wherein the processor is configured to: receive the proportion of the voltage of the potentiometer; determine a softness of the person's skin as a function of the change in the proportion of the voltages of the potentiometer; and adjust the fluid delivery time based on the softness of the person's skin.

Another embodiment of the first aspect further comprises: a shaft; a magnet connected to an end of the shaft; a spring connected to the end of the spring; and a Hall effect sensor positioned in a proximity of the magnet; wherein the spring and the Hall effect sensor are positioned inside the cavity where the microneedle array is positioned; wherein the shaft is positioned inside the cavity such that a head of the shaft is substantially at a same level as an opening of the cavity; wherein when a person's skin enters the cavity, the skin applies a pressure on the shaft, causing the distance between the magnet distance to change; and wherein the processor is configured to: receive voltage measurements from the Hall effect sensor; determine a softness of the person's skin as a function of the amount of the change in the voltage measurements of the Hall effect sensor; and adjust the fluid delivery time based on the softness of the person's skin.

Another embodiment of the first aspect further comprises: first and second pressure sensors positioned at substantially opposite sides of the cavity where the microneedle array is positioned; wherein the processor is configured to: receive pressure measurements from the first and second pressure sensors; compare the pressure measurements received from the first pressure sensor with the pressure measurements received from the second pressure sensor; and determine that the intradermal delivery device is not evenly positioned on a surface when the different between the pressure measurements received from the first pressure sensor and the pressure measurements received from the second pressure sensor is more than a threshold.

In another embodiment of the first aspect, the processor is configured to send the one or more signals to extend the microneedle array out of the cavity after the processor determines that the different between the pressure measurements received from the first pressure sensor and the pressure measurements received from the second pressure sensor does not exceed the threshold.

Another embodiment of the first aspect further comprises: an absorption pad positioned around a perimeter of the cavity where the microneedle array is positioned, the absorption pad made of a fabric having fluid absorption effects, wherein the processor is configured to: apply a voltage between a pair of points on the absorption pad; measure an electric current between the pair of points after the voltage is applied; and determine whether the absorption pad is wet based on the electric current, wherein when the absorption pad between the pair of points is dry, the electric current between the pair of points is less than or equal to a threshold, and wherein when the absorption pad between the pair of points is wet, the electric current between the pair of points is larger than the threshold.

Another embodiment of the first aspect further comprises an absorption pad positioned around a perimeter of the cavity where the microneedle array is positioned, the absorption pad made of a hydrochromic material that changes color when the absorption pad gets wet.

Another embodiment of the first aspect further comprises: a fluid compartment insertion window through which the fluid compartment is inserted in the intradermal delivery device, wherein the fluid compartment insertion window is permanently sealed after the fluid compartment is inserted in the intradermal delivery device.

Another embodiment of the first aspect further comprises a fluid compartment insertion window through which the fluid compartment is inserted in the intradermal delivery device at a time of the delivery of the fluid into the person's skin.

Another embodiment of the first aspect further comprises: a speaker; wherein the processor is configured to: receive one or more signals to play music; and play a set of musical notes in response to receiving the one or more signals to play music.

Another embodiment of the first aspect further comprises: a plurality of light sources; wherein the processor is configured to: receive one or more signals to create lighting patterns; and in response to receiving the one or more signals to create lighting patterns, turning the plurality of light sources on and off to create a set of lighting patterns.

Another embodiment of the first aspect further comprises: a set of one or more landings edges on the housing; and a microneedle array support structure comprising a movable shaft and a ridge; wherein the landings edges are positioned to come into contact with the microneedle array support structure's ridge when the microneedle array is extended out of the cavity, preventing the microneedle array from penetrating more than a predetermined distance into the person's skin.

Another embodiment of the first aspect further comprises: a closed air compartment; an air activated piston positioned at one end of the closed air compartment, the air activated piston positioned between the closed air compartment and the fluid compartment; a piercing needle positioned on the air activated piston; a fluid transfer pipe connecting the fluid compartment to a fluid reservoir that provides the fluid to the microneedle array; wherein the air pump is configured to pump air into the closed air compartment causing the piercing needle on the air activated piston to pierce a hole into the fluid compartment through which the fluid is moved into the fluid transfer pipe.

Another embodiment of the first aspect where the pump is peristaltic pump, further comprises: a piston; a piercing needle positioned on the piston; a fluid transfer pipe connecting the fluid compartment to a fluid reservoir that provides the fluid to the microneedle array; wherein the peristaltic pump is configured to move the piston causing the piercing needle on the piston to pierce a hole into the fluid compartment through which the fluid is moved into the fluid transfer pipe.

In a second aspect, an intradermal fluid delivery device comprises: a housing; a fluid compartment configured to hold a quantity of fluid; a microneedle array configured to deliver the fluid into a person's skin, the microneedle array positioned in a cavity of the housing; an actuator configured to push the fluid out of the fluid compartment and into the microneedle array; a processor configured to: receive a fluid delivery time indicating an amount of time required for the delivery of the fluid into the person's skin, wherein the fluid delivery time comprises a plurality of fluid delivery periods and a plurality of fluid stoppage periods, wherein each fluid delivery period is followed by a fluid stoppage period, and wherein durations of at least two fluid delivery periods in the plurality of fluid delivery periods are different from each other; receive one or more signals to start delivering the fluid into the person's skin; send one or more signals to extend the microneedle array out of the cavity in response to receiving the one or more signals to start delivering the fluid into the person's skin; send a set of one or more signals to the actuator at a beginning of each fluid delivery period to start pushing the fluid from the fluid compartment into the microneedle array; send a set of one or more signals to the actuator to stop the actuator at a beginning of each fluid stoppage period; and send one or more signals to retract the microneedle array into the cavity at an end of a last fluid delivery period in the plurality of fluid delivery periods.

The above description presents the best mode contemplated for carrying out the present embodiments, and of the manner and process of practicing them, in such full, clear, concise, and exact terms as to enable any person skilled in the art to which they pertain to practice these embodiments. The present embodiments are, however, susceptible to modifications and alternate constructions from those discussed above that are fully equivalent. Consequently, the present invention is not limited to the particular embodiments disclosed. On the contrary, the present invention covers all modifications and alternate constructions coming within the spirit and scope of the present disclosure. For example, the steps in the processes described herein need not be performed in the same order as they have been presented and may be performed in any order(s). Further, steps that have been presented as being performed separately may in alternative embodiments be performed concurrently. Likewise, steps that have been presented as being performed concurrently may in alternative embodiments be performed separately.

What is claimed is:

1. An intradermal fluid delivery device, comprising:
   a housing;
   a fluid compartment configured to hold a quantity of fluid;
   a microneedle array configured to deliver the fluid into a person's skin, the microneedle array positioned in a cavity of the housing;
   an air pump configured to push the fluid out of the fluid compartment and into the microneedle array; and
   a processor configured to:
      receive a fluid delivery time indicating an amount of time required for a delivery of the fluid into the person's skin, wherein the fluid delivery time comprises a plurality of fluid delivery periods and a plurality of fluid stoppage periods, and wherein durations of at least two fluid delivery periods in the plurality of fluid delivery periods are different from each other;
      receive one or more signals to start delivering the fluid into the person's skin;
      send one or more signals to extend the microneedle array out of the cavity in response to receiving the one or more signals to start delivering the fluid into the person's skin;
      send a set of one or more signals to the air pump at a beginning of each fluid delivery period to turn the air pump on and start pushing the fluid from the fluid compartment into the microneedle array;
      send a set of one or more signals to the air pump to stop the air pump at a beginning of each fluid stoppage period; and
      send one or more signals to retract the microneedle array into the cavity at an end of the fluid delivery time.

2. The intradermal delivery device of claim 1, wherein durations of at least two fluid stoppage periods in the plurality of fluid stoppage periods are different from each other.

3. The intradermal delivery device of claim 1 further comprising:
   a wireless transceiver,
   wherein the processor is configured to:
      receive the one or more signals to start delivering the fluid into the person's skin from an external electronic device that is communicatively coupled to the processor through the wireless transceiver.

4. The intradermal delivery device of claim 1 further comprising:
   a set of one or more activation buttons,
   wherein the processor is configured to:
      receive the one or more signals to start delivering the fluid into the person's skin when one of the activation buttons in the set of activation buttons is depressed.

5. The intradermal delivery device of claim 1 further comprising:
   a wireless transceiver,
   wherein the processor is configured to:
      determine, after the end of the fluid delivery time, whether the person has opted in for reporting a location of the intradermal delivery device; and
      send the location of the intradermal delivery device to one or more external electronic devices through the wireless transceiver when the person is determined to have opted in for the reporting.

6. The intradermal delivery device of claim 1, wherein the cavity is a first cavity, the intradermal delivery device further comprising:
   a second cavity in the housing;
   a light source and a light sensor positioned on opposite sides of an interior of the second cavity, wherein the light source is positioned to direct light to the light sensor, and wherein the light source and the light sensor are positioned such that when a person's skin enters the second cavity, at least a portion of the light directed from the light source to the light sensor is blocked by the person's skin;
   wherein the processor is configured to:
      receive light measurements from the light sensor;
      determine a softness of the person's skin as a function of an amount of the light source's light that is blocked by the person's skin; and
      adjust the fluid delivery time based on the softness of the person's skin.

7. The intradermal delivery device of claim 1 further comprising:
   a light source and a light sensor positioned on opposite sides of an interior of the cavity where the microneedle array is positioned, wherein the light source is positioned to direct light to the light sensor, and wherein the light source and the light sensor are positioned such that when a person's skin enters the cavity, at least a portion of the light directed from the light source to the light sensor is blocked by the person's skin;
   wherein the processor is configured to:
      receive light measurements from the light sensor;
      determine a softness of the person's skin as a function of an amount of the light source's light that is blocked by the person's skin; and
      adjust the fluid delivery time based on the softness of the person's skin.

8. The intradermal delivery device of claim 1 further comprising:
   a shaft;
   a spring connected to the shaft; and
   a pressure sensor connected to the spring;
   wherein the spring and the pressure sensor are positioned inside the cavity where the microneedle array is positioned;

wherein the shaft is positioned inside the cavity where the microneedle array is positioned such that a head of the shaft is substantially at a same level as an opening of the cavity;

wherein when a person's skin enters the cavity, the person's skin applies a pressure on the shaft, causing the shaft to press the spring, causing the spring to apply a pressure to the pressure sensor; and wherein the processor is configured to:
receive pressure measurements from the pressure sensor;
determine a softness of the person's skin as a function of an amount of the pressure applied by the spring to the pressure sensor; and
adjust the fluid delivery time based on the softness of the person's skin.

9. The intradermal delivery device of claim 1 further comprising:
a shaft;
a spring connected to the shaft; and
a potentiometer connected to the spring, wherein the potentiometer comprises a moving contact that is configured to move and change a voltage proportion of a voltage divider of the potentiometer;
wherein the spring and the potentiometer are positioned inside the cavity where the microneedle array is positioned;
wherein the shaft is positioned inside the cavity such that a head of the shaft is substantially at a same level as an opening of the cavity;
wherein when a person's skin enters the cavity, the person's skin applies a pressure on the shaft, causing the shaft to press the spring, causing the spring to move the potentiometer's contact and change the voltage proportion of the potentiometer; and
wherein the processor is configured to:
receive the voltage proportion of the voltage of the potentiometer;
determine a softness of the person's skin as a function of the change in the voltage proportion of the potentiometer; and
adjust the fluid delivery time based on the softness of the person's skin.

10. The intradermal delivery device of claim 1 further comprising:
a shaft;
a magnet connected to an end of the shaft;
a spring connected to the end of the shaft; and
a Hall effect sensor positioned in a proximity of the magnet;
wherein the spring and the Hall effect sensor are positioned inside the cavity where the microneedle array is positioned;
wherein the shaft is positioned inside the cavity such that a head of the shaft is substantially at a same level as an opening of the cavity;
wherein when a person's skin enters the cavity, the person's skin applies a pressure on the shaft, causing the distance between the magnet and the Hall effect sensor to change; and
wherein the processor is configured to:
receive voltage measurements from the Hall effect sensor;
determine a softness of the person's skin as a function of an amount of change in the voltage measurements of the Hall effect sensor; and
adjust the fluid delivery time based on the softness of the person's skin.

11. The intradermal delivery device of claim 1 further comprising:
first and second pressure sensors positioned at substantially opposite sides of the cavity where the microneedle array is positioned;
wherein the processor is configured to:
receive pressure measurements from the first and second pressure sensors;
compare the pressure measurements received from the first pressure sensor with the pressure measurements received from the second pressure sensor; and
determine that the intradermal delivery device is not evenly positioned on a surface when a difference between the pressure measurements received from the first pressure sensor and the pressure measurements received from the second pressure sensor is more than a threshold.

12. The intradermal delivery device of claim 11, wherein the processor is configured to send the one or more signals to extend the microneedle array out of the cavity after the processor determines that the difference between the pressure measurements received from the first pressure sensor and the pressure measurements received from the second pressure sensor does not exceed the threshold.

13. The intradermal delivery device of claim 1 further comprising:
an absorption pad positioned around a perimeter of the cavity where the microneedle array is positioned, the absorption pad made of a material having fluid absorption effects;
wherein the processor is configured to:
apply a voltage between a pair of points on the absorption pad;
measure an electric current between the pair of points after the voltage is applied; and
determine whether the absorption pad is wet based on the electric current between the pair of points, wherein when the absorption pad between the pair of points is dry, the electric current between the pair of points is less than or equal to a threshold, and wherein when the absorption pad between the pair of points is wet, the electric current between the pair of points is larger than the threshold.

14. The intradermal delivery device of claim 1 further comprising an absorption pad positioned around a perimeter of the cavity where the microneedle array is positioned, the absorption pad made of a hydrochromic material that changes color when the absorption pad gets wet.

15. The intradermal delivery device of claim 1 further comprising:
a fluid compartment insertion window through which the fluid compartment is inserted in the intradermal delivery device, wherein the fluid compartment insertion window is permanently sealed after the fluid compartment is inserted in the intradermal delivery device.

16. The intradermal delivery device of claim 1 further comprising a fluid compartment insertion window through which the fluid compartment is inserted in the intradermal delivery device at a time of the delivery of the fluid into the person's skin.

17. The intradermal delivery device of claim 1 further comprising:
a speaker;
wherein the processor is configured to:
receive one or more signals to play music; and
play a set of musical notes in response to receiving the one or more signals to play music.

18. The intradermal delivery device of claim 1 further comprising:
a plurality of light sources;
wherein the processor is configured to:
receive one or more signals to create lighting patterns; and
in response to receiving the one or more signals to create lighting patterns, turning the plurality of light sources on and off to create a set of lighting patterns.

19. The intradermal delivery device of claim 1 further comprising:
a set of one or more landings edges on the housing; and
a microneedle array support structure comprising a movable shaft and a ridge;
wherein the landings edges are positioned to come into contact with the microneedle array support structure's ridge when the microneedle array is extended out of the cavity, preventing the microneedle array from penetrating more than a predetermined distance into the person's skin.

20. The intradermal delivery device of claim 1, further comprising:
a closed air compartment;
an air activated piston positioned at one end of the closed air compartment, the air activated piston positioned between the closed air compartment and the fluid compartment;
a piercing needle positioned on the air activated piston; and
a fluid transfer pipe connecting the fluid compartment to a fluid reservoir that provides the fluid to the microneedle array;
wherein the air pump is configured to pump air into the closed air compartment causing the piercing needle on the air activated piston to pierce a hole into the fluid compartment through which the fluid is moved into the fluid transfer pipe.

* * * * *